United States Patent [19]
Fong et al.

[11] Patent Number: 6,051,428
[45] Date of Patent: Apr. 18, 2000

[54] RAPID PRODUCTION OF AUTOLOGOUS TUMOR VACCINES

[75] Inventors: Yuman Fong, New York; Howard Federoff; Joseph D. Rosenblatt, both of Rochester, all of N.Y.

[73] Assignees: Sloan-Kettering Institute for Cancer Research, New York; University of Rochester, Rochester, both of N.Y.

[21] Appl. No.: 09/045,476

[22] Filed: Jan. 20, 1998

Related U.S. Application Data

[60] Provisional application No. 60/044,005, Mar. 21, 1997.
[51] Int. Cl.[7] ............................ C12N 15/63; C12N 15/12; C12N 15/38; A61K 39/245
[52] U.S. Cl. ...................... 435/456; 435/320.1; 536/23.5; 536/23.72; 424/199.1; 424/231.1
[58] Field of Search .............................. 424/93.21, 199.1, 424/231.1; 435/320.1, 456; 536/23.5, 23.72

[56] References Cited

FOREIGN PATENT DOCUMENTS

96/29421  9/1966  WIPO .
97/00085  1/1997  WIPO .

OTHER PUBLICATIONS

Parijs et al. Homeostasis and self–tolerance in the immune system: Turning lymphocytes off. Science vol. 280 pp. 243–248, 1998.

Hellstrom et al. Tumor vaccines–A reality at last? Journal of Immunotherapy vol. 21 pp. 119–126, 1998.

Vieweg et al. considerations for the use of cytokine–secreting tumor cell preparations for cancer treatment. Cancer Investigation vol. 13 pp. 193–201, 1995.

Stevenson Tumor Vaccines FASEB J. vol. 5 pp. 2250–2257, 1991.

Tung, et al., "Rapid Production of Interleukin–2–Secreting Tumor Cells by Herpes Simplex Virus–Mediated Gene Transfer: Implications for Autologous Vaccine Production.", vol. 7, 1996, pp. 2217–2224.

Kutubuddin, et al., "Eradication of preexisting murine tumor using herpes amplicon vectors.", Cancer Gene Therapy vol. 4, No. 6, Nov. 1997—Dec. 1997, p. S26.

Dranoff, et al., "Vaccination with irradiated tumor cells engineered to secrete murine granulocyte–macrophage colony–stimulating factor stimulates potent, specific, and long–lasting anti–tumor immunity.", 1993, pp. 3539–3543.

Karpoff, et al., "Prevention of Hepatic Tumor Metastases in Rats with Herpes Viral Vaccines and y–Interferon.", vol. 99, No. 4, Feb. 1997, pp. 799–804.

Vieweg, et al., "Immunotherapy of prostate cancer in the Dunning rat model: use of cytokine gene modified tumor vaccines.", Medline for Cancer Res 54: 1760–1765 (1994).

Iwanuma, et al., "Induction of tumor–specific cytotoxic T lymphocytes and natural killer cells by tumor cells transfected with the interleukin–2 gene.", Medline for Cancer Immunol Immunother 40: 17–23 (1995).

Abe, et al., "Antitumor effect induced by granulocyte/macrophage–colony–stimulating factor gene–modified tumor vaccination: comparison of adenovires– and retrovirus–medicated genetic transduction." Medline for J Cancer Res Clin Oncol 121: 587–592 (1995).

*Primary Examiner*—John S. Brusca

[57] ABSTRACT

An autologous vaccine to tumor cells is produced by transducing the tumor cells with a herpes simplex virus amplicon containing the gene for an immunomodulatory protein to provide transient expression of the immunomodulatory protein by the cells. The tumor cells may transduced with the herpes simplex amplicons ex vivo or in vivo. Suitable immunomodulatory proteins include cytokines, for example, interleukins, interferons, and chemokines such as RANTES; intercellular adhesion molecules, for example ICAM-1 and costimulatory factors such as B7.1. The tumor cells may also be transduced with one or more species of amplicon containing genes for two or more different immunomodulatory proteins.

40 Claims, 14 Drawing Sheets

RAPID PRODUCTION OF AUTOLOGOUS TUMOR VACCINES

This application is a regular application filed under 35 USC § 111(a), claiming benefit of US Provisional Application 60/044,005 filed Mar. 21, 1997.

The work described in this application was supported in part by NIH Grants Nos. CA76416, CA72632, HD 31300, DK53160, and PO1 CA59326. The United States government may have certain rights in this invention.

BACKGROUND OF THE INVENTION

Cytokine gene transfer to tumor cells has been used to increase local production of these immune modulating proteins, with the aim of enhancing tumor immunogenicity and consequent host recognition and elimination of tumor (Dranoff et al. 1993; Gansbacher et al. 1992). Production of irradiated, non-dividing tumor cells secreting cytokines such as Interleukin-2 (IL-2), gamma-interferon (γ-IFN), or granulocyte macrophage-colony stimulating factor (GM-CSF) represents a potential therapeutic strategy for treatment of malignant disease (Saito et al. 1994; Dranoff et al. 1993; Gansbacher et al. 1992), and one that is currently being evaluated in clinical trials (Lotze et al. 1994; Seigler et al. 1994; Rosenberg et al. 1992). Many methods have been examined for gene transfer (Davidson et al. 1993; Drazan et al. 1994; Yang et al. 1995; Paquereau & Le Cam, 1992; Jamagin et al. 1992); the most successful have been those using retroviral vectors (Dranoff et al. 1993; Gansbacher et al. 1992).

An impediment to the production of autologous tumor vaccines has been logistic problems surrounding gene transfer to freshly harvested tumors. The most widely utilized approach for gene transfer to tumors relies on retroviral vectors, which are relatively inefficient and require replicating cells for gene expression (Wilson et al. 1988). The production of an autologous vaccine using retroviral vectors requires placing harvested tumor in tissue culture before in vitro transduction, selection, and isolation of the minority of cells in which gene transfer was successful. Such a process is therefore lengthy, expensive, and fraught with technical problems of establishing and maintaining primary cell culture. These difficulties have forced investigators to examine as alternative vaccine strategies the administration of established allogeneic cytokine-secreting tumor cell lines (Patel et al. 1994), use of other vectors for gene transfer such as adenoviral vectors (Drazan et al. 1994; Yang et al. 1995), or the administration of cytokine-producing fibroblast cell lines along with the autologous tumor cells (Lotze et al. 1994).

It is an object of the present invention to provide a method for rapid production of autologous tumor vaccines which can be completed within hours, for example in less than four hours, permitting rapid treatment of tumor patients.

It is a further object of the invention to provide a method for rapid production with autologous tumor vaccines which can be applied to tumor cells in vivo without requiring surgical removal of tumor material.

It is still a further object of the present invention to provide compositions useful in the methods of the invention.

SUMMARY OF THE INVENTION

In accordance with the present invention an autologous vaccine to tumor cells is produced by transducing the tumor cells with a herpes simplex virus amplicon containing the gene for an immunostimulating protein to provide transient expression of the immunostimulating protein by the cells. The tumor cells may be transduced with the herpes simplex amplicons ex vivo or in vivo. Preferred immunostimulating protein used in the method of the invention include cytokines such as RANTES (a chemokine), interleukin-2 and GM-CSF, intracellular adhesion molecules such as ICAM-1, and costimulatory factors such as B7.1.

A particularly important aspect of the present invention is the fact that tumor cells may be readily transduced with a combination of amplicons containing genes for two or more different immunostimulating proteins, for example interleukin-2 and interleukin 12 or RANTES and B7.1. This greatly facilitates the production of multiply-transdcued cells for multi-targeted therapy.

DETAILED DESCRIPTION OF THE INVENTION

Figure 1A:
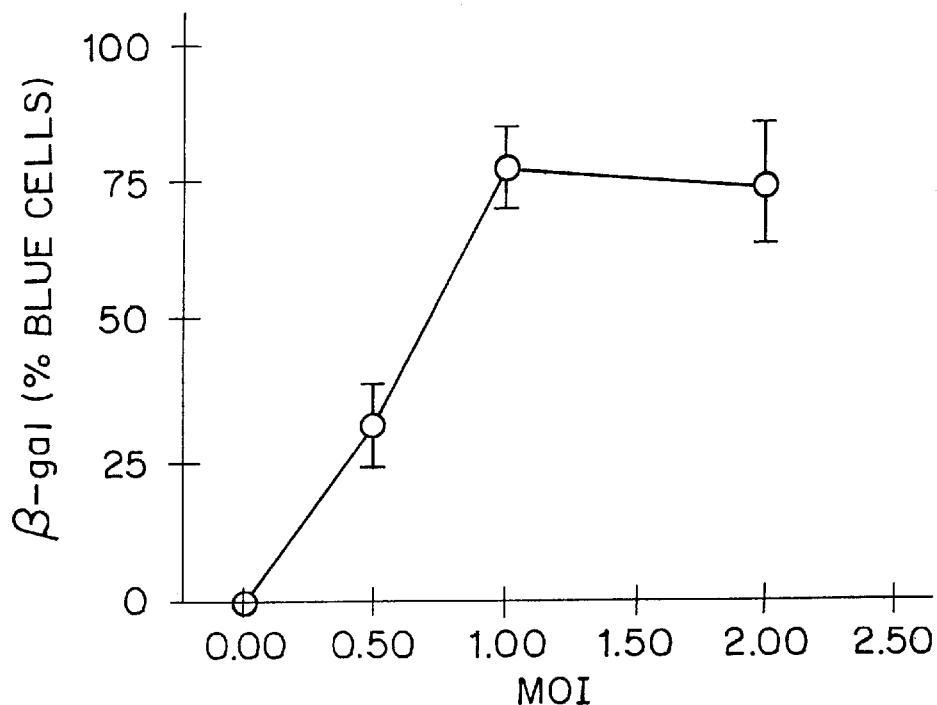
FIGS. 1A–E summarize the results of studies on the efficiency of gene transfer using HSV amplicons according to the invention.

Herpes simplex virus (HSV) is a DNA virus capable of rapidly and efficiently infecting a wide variety of cell types (Leib & Olivo, 1993; Geller & Federoff, 1991). Plasmid-based viral vectors derived from HSV, termed amplicons, are easily constructed and packaged into viral particles. The present invention uses herpes simplex virus amplicons containing genes encoding for immunomodulating proteins to transduce tumor cells with high efficiency either ex vivo or in vivo.

As used herein, the term "immunostimulating proteins" refers to a class of immunomodulating protein or peptide molecules which, when expressed by a target cell, enhance the development of an immune response to that cell. The term includes cytokines, including chemokines; intercellular adhesion molecules, and costimulatory factors necessary for activation of B or T cells.

Cytokines which may be used as immunomodulating proteins in the invention include but are not limited to interleukins, such as interleukin-2 (IL-2), interleukin-12 (IL-12); interferons, for example gamma interferon (γ-IFN), granulocyte macrophage colony stimulating factor (GM-CSF) and tumor necrosis factor alpha (TNF-α). The immunomodulating protein may also be a chemokine such as RANTES, which is a β or C-C chemokine, that functions as a chemoattractant and activator for monocytes and macrophages. Other C-C chemokines, such as MCP-1, -2, and -3, DC-CK1 and MIP-1α, -3α, -β and -3β, and α or C-X-C chemokines such as IL-8, SDF-1β, 8DF-1α, GRO, PF-4 and MIP-2 could also be used. Other chemokines useful in the method are C family, for example lympotactin and CX3C family, for example fractal kine, chemokines.

Intercellular adhesion molecules are transmembrane proteins within the Ig superfamily that act as mediators of adhesion of leukocytes to vascular endothelium and to one another. A preferred intercellular adhesion molecule for use in the invention is ICAM-1 (also known as CD54), although other cell adhesion molecules that binds to T or B cells, including ICAM-2 and -3 could also be used.

Costimulatory factors which may be used as the immunomodulatory protein in the present invention are cell surface molecules other than an antigen receptor and its ligand that are required for an efficient response of lymphocytes to an antigen. Examples of such costimulatory factors include B7 (also known as CD80).

HSV vectors systems are efficient vehicles for gene transfer to tumor cells. In experiments using HSVlac, over 50% of the target cells are transduced using an MOI of 1. The efficiency of transduction is further reflected by the high levels of IL-2 produced by HSVil2-transduced cells. Production of levels greater than 1 $\mu g/10^6$ cells/24 hour was found, which is more than 30 times that achieved by retrovirally-produced vaccines (Patel et al. 1994; Gansbacher et al. 1992). Additionally, the data from the experiments with HSVil2-transduced human tumors demonstrate that successful HSV-mediated gene transfer to freshly-isolated tumor cells can also be used to produce genetically-engineered cells that secrete significant amounts of bioactive IL-2.

A major advantage of using HSV vectors for gene transfer is the ability to transduce non-replicating or slowly replicating cells (Geller & Federoff, 1991). This physical property of HSV translates into important clinical advantages. Freshly isolated tumor cells may be transduced without the need to provide a tissue culture environment conducive to cell replication. This advantage is clearly demonstrated by the rapidity with which freshly harvested human tumors were transduced in the current experiments. Within 20 min, efficient gene transfer was produced, suggesting that vaccines prepared by this method could be ready for administration to patients within a single operative procedure. That HSV-mediated gene transfer is independent of cell division and is supported by a transduction efficiency that was not reduced by prior irradiation of tumor cells. Thus, gene transfer to tumor cells may be performed either before or after radiation according to irradiation source availability, providing greater flexibility in the clinical care of patients.

HSV-immunomodulatory protein amplicons and cells transduced with such amplicons are able to confer specific antitumor immunity that protects against tumor growth in vivo. The amplicons may be introduced indirectly by administration of transduced cells into a living organism or patient (mammalian, including human). Alternatively, the HSV-immunomodulatory protein amplicon may be introduced directly into tumor tissue (e.g. by peritumoral injection) within a living organism or patient to generate an antitumor immunity which leads to reduction in tumor size. This latter approach is useful, for example, in the case of inoperable tumors.

In accordance with the present invention, HSV-immunomodulatory protein amplicons may be administered, directly or indirectly, as individual species in order to provide a therapeutic and/or prophylactic benefit. For example, as described in the examples set forth herein, it has been determined that administration of HSV-immunomodulatory protein amplicons encoding cytokines such as IL2, GM-CSF and RANTES, intercellular adhesion molecules such as ICAM-1 and costimulatory factors such as B7.1 all provide therapeutic benefit in the form of reduction or preexisting tumor size, a vaccine-effect protecting against tumor growth after a subsequent challenge, or both.

HSV-immunomodulatory protein amplicons may also be administered, directly or indirectly, with other species of HSV-immunomodulatory transduced cells or in combination with cytokine therapy. Such administrations may be concurrent or they may be done sequentially. Thus, in one embodiment of the invention, HSV amplicons or cells transformed with an HSV amplicon encoding an immunomodulatory protein are injected into a living organism or patient, after a pre-treatment with a therapeutically effective amount of a cytokine. Both HSVil2 and HSVgm-csf have been shown to have increased efficacy when administered following a pretreatment of γ-IFN.

In another embodiment of the invention, populations of HSV amplicons or cells transduced with HSV amplicons encoding a plurality of different immunomodulatory proteins may be coadministered to the subject. For example, populations of tumor cells transduced with HSVil2 and HSVil12 may be coadministered As shown in the examples, such coadministration is somewhat more effective than administration of individual populations. Coadministration of cells expressing these two cytokines appears to be most effective, however, when a single population of cells that has been transduced with two different cytokine-encoding amplicons is used. Such populations can be made either with separate amplicons species, one encoding each immunomodulatory protein, or which a single amplicon species encoding a plurality of immunomodulatory proteins.

The ability to use separate amplicon species to transduce cells to produce multiple immunomodulatory proteins is a major advantage over prior methods, such as use of retroviral vectors, for introduction of genetic material into target cells. In these prior methods, the frequency of transduction is so low that no reasonable percentage of cells would be transduced with multiple genes if two or more separate viral vectors were used. Therefore, therapies of this type require the preparation of a unique and complicated construct containing multiple genes for each separate form of multi-targeted gene therapy. Using the method of the present invention, however, each target gene can be constructed in its own amplicon, and multi-transduced cells produced by simply mixing combinations of desired amplicon species.

Another example of the benefits of coadministration of a plurality of HSV-immunomodulatory protein amplicons is seen with the chemokine RANTES and the costimulatory factor B7.1, Although peritumoral administration of either HSVB7.1 or HSVrantes resulted in tumor rejection is a significant number of test subjects, when HSV amplicons encoding these two immunomodulatory proteins are combined, an increased number of animals reject the tumors.

Thus, the present invention provides a method for production of an autologous vaccine to tumor cells comprising transducing the tumor cells with a herpes simplex virus amplicon containing the gene for an immunomodulatory protein to provide transient expression of the immunomodulatory protein by the cells. The tumor cells may be transduced with the herpes simplex amplicons ex vivo or the may be transduced with the herpes simplex amplicons in vivo. The tumor cells may be transduced with one or more species of amplicon containing the genes for more than one kind of immunomodulatory protein and expressing more than one kind of immunomodulatory protein.

The invention also provides a method for inducing a protective immune response to tumor cells in a patient (animal or human) comprising the step of transducing the tumor cells with a herpes simplex virus amplicon containing the gene for at least one immunomodulatory protein to provide transient expression of the immunomodulatory protein by the cells. The tumor cells may be transduced with the amplicon ex vivo, in which case the method further comprises the step of introducing the transduced tumor cells into the patient. The tumor cells may also be transduced in vivo by injecting the HSV amplicons into the site of the tumor cells.

The invention also provides a method for production of an autologous vaccine to tumor cells comprising transducing the tumor cells with one or more species herpes simplex virus amplicon containing the gene for an immunomodulatory protein and at least one additional therapeutic gene to provide transient expression of the immunomodulatory protein and the therapeutic gene product by the cells. As noted from the specific examples in this application, the additional gene may by a gene encoding a second immunomodulatory protein. However, the therapeutic gene product is not limited to immunomodulatory proteins, and may include any protein or peptide which it is desirable to have expressed by autologous tumor vaccine cells. Thus, for example, the gene might code for an enzyme which is used for pro-drug conversion (for example, thymidine kinase), or for a protein which promotes apoptosis (BAX or $BCLX_s$).

The invention also provides HSV amplicons which contain the gene for one or more immunomodulatory proteins, and cells transduced with such amplicons.

The invention will now be further described with reference to the specific examples which follow. It should be understood, however, that these are merely offered as examples and are not intended to limit the scope of the invention. Thus, other immunomodulatory proteins not specifically mentioned, and other combinations of immunomodulatory proteins, including combination of three or more immunomodulatory proteins may be used and are considered to be with in the scope of the present invention as defined in the claims of this application.

EXAMPLE 1

Herpes viral vectors: construction and packaging: The replication defective HSV amplicon vector expressing human IL-2 was constructed by directionally cloning the gene, excised from r-IL-2 (Saito et al. 1994) with Sac I and Eco RI, into HSV PrPUC (Bergold et al. 1993) digested with the same enzymes. The HSV vector expressing β-galactosidase (HSVlac) has been previously described (Geller & Breakefield, 1988). Both amplicon vectors were packaged as previously described (Federoff, 1996; Geller & Breakefield, 1988). HSVPrPUC contains the HSV immediate early 4/5 promoter, a multiple cloning site and SV40 A sequence and has been described previously (Paterson & Everett, 1990; Johnson et al. 1992; Xu et al. 1994; Linnik et al. 1995; Bergold et al. 1993). The RR1 cells used for packaging HSV amplicons were maintained in Dulbecco's modified Eagle's medium (DMEM) containing high glucose (HG, 4.5 g/l), 10% FCS, 1% penicillin/streptomycin and 400 μg/ml of bioactive geneticin (G418, Gibco) at 37° C., 5% $CO_2$. RR1 cells are BHK cells stably transfected with the HSV IE3 gene and were obtained from Dr. Paul Johnson (Johnson et al. 1992). D30 EBA helper virus was prepared by growth on RR1 cells. D30EBA is a strain 17 derived IE3 mutant deleted from codons 83 to 1236 and was obtained from Dr. Roger Everett (Paterson & Everett, 1990). To package amplicon vectors, $3 \times 10^6$ RR1 cells were plated in media containing 10% FCS and 4 h later were transfected by adding 40 μl of Lipofectin (Gibco-BRL), waiting 5 min and then adding the amplicon DNA solution dropwise (30 μg at 1 μg/μl in DMEM). Six hours later, plates were fed with media containing 5% FCS. Approximately 20 h after transfection, D30 EBA virus in 50–100 μl was added to achieve a multiplicity of infection (MOI) of 0.2. Five ml of complete media with 5% FCS were added to each plate after 1 h. Amplicon virus stocks were harvested 2 days later. After overnight storage at −70° C., fresh RR1 cells ($4 \times 10^6$ cells/60 mm plate) were infected with sonicated and warmed (34° C.) virus stock. Two days later, the stocks were harvested and stored for subsequent use. HSVlac virus stocks were titered by an expression assay. In brief, NIH 3T3 cells were plated ($2 \times 10^5$ cells per well of 24 well plate) and infected with increasing volumes of an HSV amplicon virus stock in duplicate. Twenty-four h after infection, cells were fixed and stained with the chromogenic substrate 5-bromo-4-chloro-3-indolyl β-D-galactoside (X-gal) using standard methods (Geller & Breakefield, 1988). The number of X-gal+ (blue) cells were counted. Titers are expressed as the number of blue forming units/ml. The D30 EBA helper virus in each stock was titered by plaque assay on RR1 cells, and HSVil2 was titered by a slot blot assay as described previously (Geschwind et al. 1994). For slot blot analysis, viral DNA was extracted from packaged virus by phenol/chloroform twice, ethanol precipitated with single strand calf thymus DNA as carrier, denatured at room temperature with 0.2 N NaOH, 0.5 M NaCl for ten minutes and loaded on nylon membrane with a slot blot apparatus. The membrane was then baked for 2 hours at 65° C., and probed with a [$^{32}$P]-labeled 435 bp SspI and PvuI fragment containing part of the β-lactamase gene from pBR322 (nucleotides 3733–4168). After stringent washing (0.1× SSC twice for 15 minutes), blots were exposed to X-Ray film and various timed exposures taken and densitometrically scanned (LKB Ultrascan). Band densities between HSVlac and HSVil2 were compared and the titer of HSVil2 calculated from the density relative to HSVlac given that this latter amplicon was titered by an expression assay (blue forming units on NIH 3T3 cells). The titers of HSVil2 are expressed as particles/ml.

Titers of amplicon stocks: HSVlac titers were between $2 \times 10^6$ blue forming units/ml as titered by expression and X-gal histochemistry on NIH 3T3 cells. The HSVil2 titers, determined by slot blot (described above), were between 0.8 and $2 \times 10^6$ particles/ml. D30EBA titers in stocks ranged between $5\times10^6$ to $6\times10^7$ plaque forming units/ml. Recombination for wildtype revertants was monitored by plaque assay on Vero cells and occurred at a frequency of $1\times10^{-6}$.

EXAMPLE 2

Murine hepatoma cells were transduced ex vivo using amplicons prepared as in example 1. Murine HEPA 1–6 hepatoma cells (ATCC, Rockville, Md.) were maintained in DMEM+HG+10% FCS. This is a non-immunogenic hepatoma cell line (Engvall et al. 1977). Cells were plated at either 2 or $10\times10^5$ cells/well for all virus expression studies. In some experiments, cells were irradiated 2 h after plating and then infected with HSV amplicon stocks. In other experiments, cells were irradiated 1 h after infection with HSV amplicon stocks. Hepatoma cells were irradiated at room temperature with a 6-mV Varian CL6-100 linear accelerator at a dose-rate of 100 rads/min. To assess the rapidity of HSV amplicon gene transfer, hepatoma cells were exposed to vector stocks for either 20 or 60 min, washed extensively and cultured. After an additional 48 h, cells were histochemically stained with X-gal (HSVlac) or media assayed for IL-2 (HSVil2). In some experiments tumor cell lysates were prepared by suspension in a solution containing 0.15 M NaCl, 50 mM Tris, 1% NP-40, 4 mM NaF, pH=8, and assayed for IL-2. Additionally, representative samples were harvested 48 hours after treatment and viable tumor cells counted.

Figure 1B:
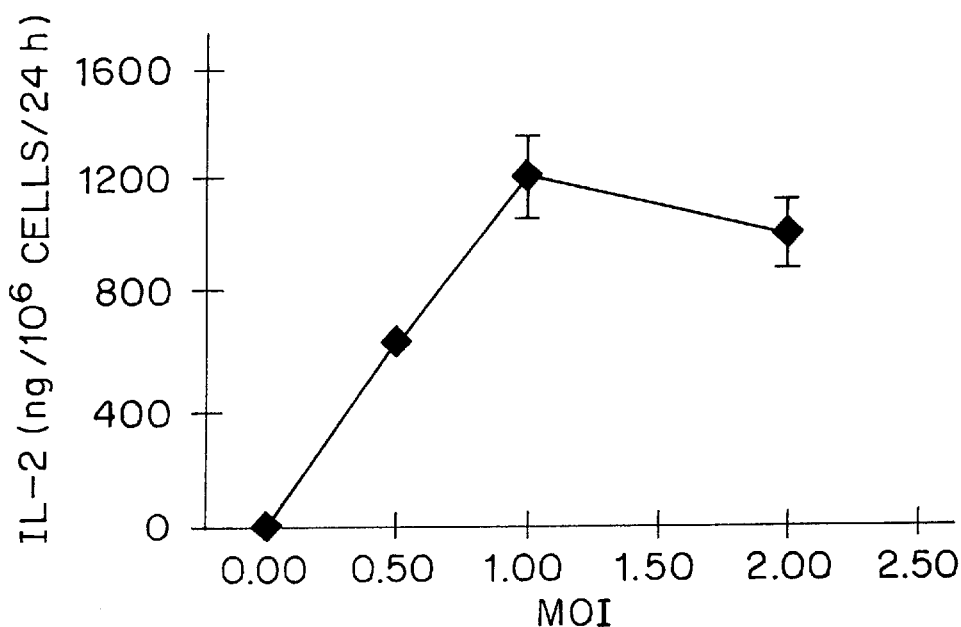
Figure 1C:
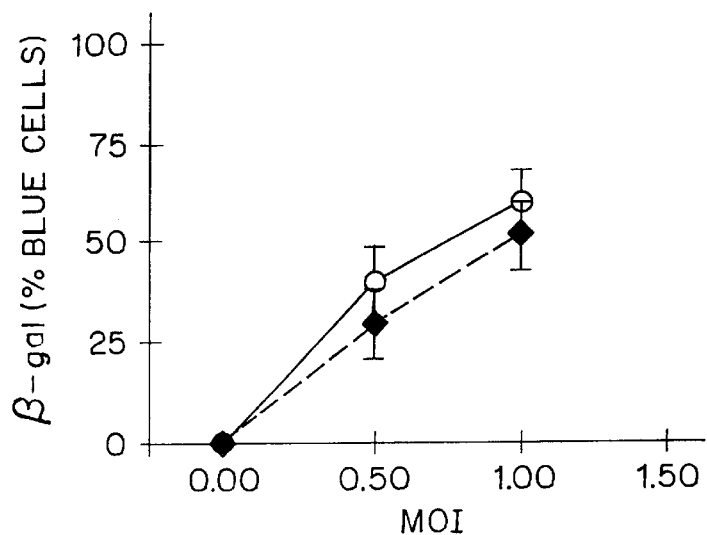
Figure 1D:
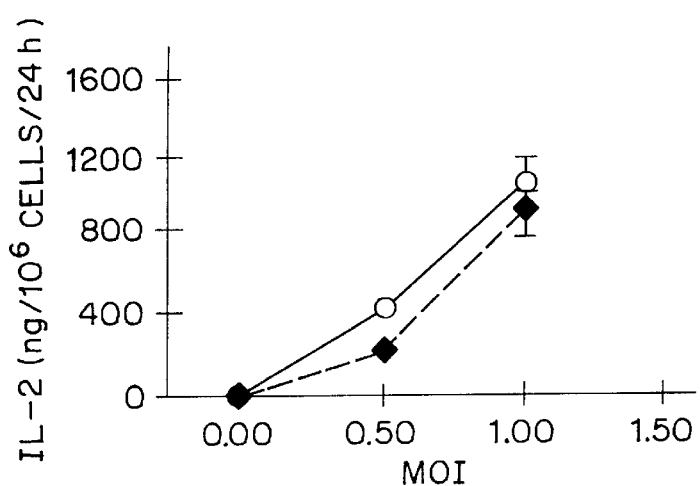

The results of these experiments on the efficiency of gene transfer according to the invention are summarized in FIG. 1A and B. As shown, both the HSVlac and HSV-IL-2 amplicon stocks gave maximum transfer efficiencies at an MOI of 1 or greater. In HSVlac infected cultures (FIG. 1A, -○-), greater than 50% of the hepatoma cells expressed the reporter gene, β-galactosidase. Fewer cells (30%) expressed β-galactosidase when infected at an MOI of 0.5. HSVil2 infected cultures (FIG. 1B, -●-, MOI-1.0) secreted $1,200\pm160$ ng/$10^6$ cells/24 hours. The immunoreactive IL-2 detected by ELISA was confirmed to be bioactive by the CML assay. Each 50 pg of immunoreactive IL-2 was equivalent to approximately 1 unit of bioactivity. The extent of gene transfer was equivalent at whether virus exposure was 20 or 60 minutes (FIGS. 1C and 1D, dashed lines=20 minute incubation, solid lines=60 minute incubation), indicating that virtually all infectious HSV virions adsorb to cells within 20 min. In addition, rapid gene transfer was not a function of MOI, since expression was comparable in 20 and 60 min exposures periods at both MOIs tested (0.5 and 1.0, FIGS. 1C and D).

Figure 1E:
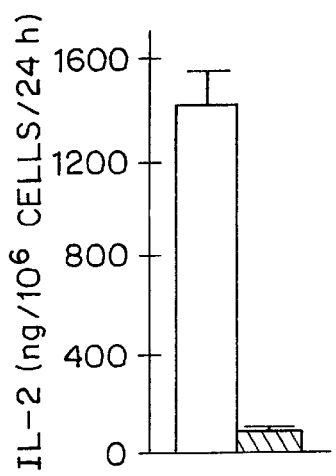

Although IL-2 secretory rates from HSVil2-infected hepatoma cells were appreciable and in the range previously demonstrated to be immunomodulatory, it was possible that additional IL-2 might remain in an intracellular compartment. To address this issue, IL-2 measurements were made on infected cell lysates and compared with the levels found in media conditioned by these cells (FIG. 1E, open bar=media, solid bar=lysates). The amount of IL-2 secreted in a 24 hour period was approximately 10-fold greater than the cellular content (media: $1400\pm100$ ng/$10^6$ cells/24 h, lysate:$100\pm9$ ng/$10^6$ cells/24 h), suggesting the that the murine hepatoma cells efficiently secreted the cytokine.

Figure 2A:
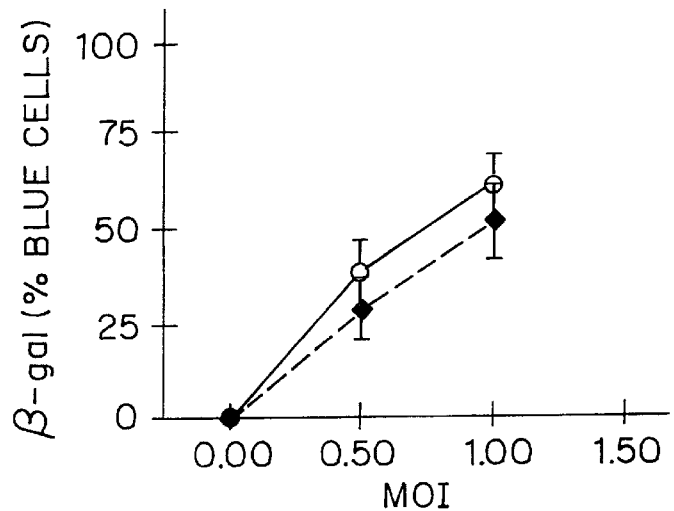
FIGS. 2A–C summarize the effects of irradiation on gene transfer efficiency.
Figure 2B:
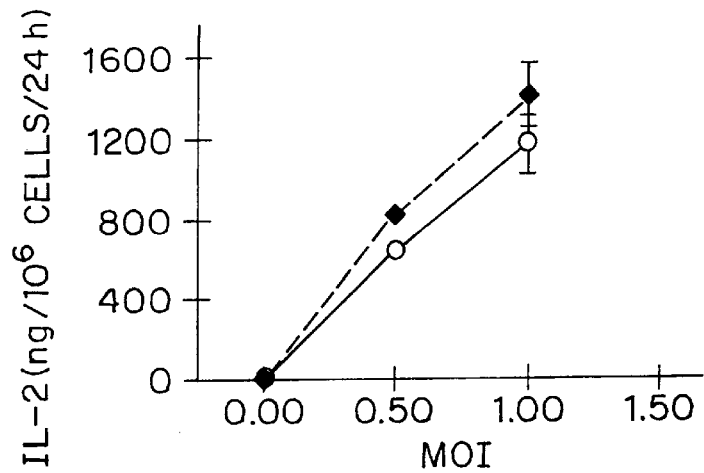
Figure 2C:
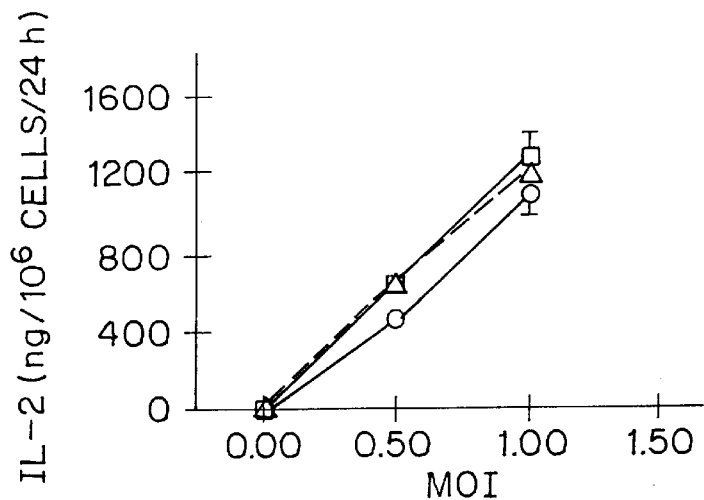

Because radiation treatment of tumor cells has been viewed as an important part of producing non-dividing tumor vaccines, the affects of the timing of cell irradiation relative to HSV infection on gene transfer efficiency was investigated. As shown in FIGS. 2A and B, irradiation prior to (broken lines) or just after (solid lines) HSV infection produced similar gene transfer efficiencies. Although there was a trend to higher gene transfer and expression levels in cells infected prior to irradiation, this difference was not significant. This trend towards higher gene transfer in cells infected prior to irradiation was not due to a difference in cell viability (Table 2). Of particular interest was the observation that cells irradiated at different doses secreted levels of IL-2 that were comparable to non-irradiated cells (FIG. 2C, ○=0 rads, □=2,000 rads, Δ=10,000 rads). Moreover, although irradiation affects cellular replication functions, it appears to have no affect on the biogenesis of secreted IL-2.

EXAMPLE 3

Human tumor cells were transduced in vitro using an amplicon containing the interleukin-2 gene produced in accordance with Example 1. This study was performed with approval and under the guidelines of the Institutional Review Board of the Memorial Sloan-Kettering Cancer Center. Tumor biopsies of approximately 5 grams were obtained from four patients undergoing liver resection for hepatobiliary malignancies. The patient characteristics are listed in Table 1. All specimens were removed prior to any vascular interruption or Pringle maneuvers. Histologic verification of tumor was obtained in all cases. Tumor specimens were immediately placed in cold (4° C.) RPMI-1640 for transport to the laboratory. Each specimen was then minced into fine pieces and treated with 0.125% trypsin/0.125% EDTA in PBS without $Ca^{++}$ or $Mg^{++}$ for 5 min. The treated tumor was then teased apart and filtered through a sterile 85 μm nylon mesh into RPMI-1640 medium (4° C.) containing 10% human serum. Freshly-isolated cells in suspension were irradiated at 10,000 rads at room temperature with a 6-mV Varian CL6-100 linear accelerator at a dose-rate of 100 rads/min. Aliquots of $10^6$ tumor cells were then infected with HSV amplicon stocks for 20 min. Aliquots of non-irradiated cells were treated similarly and served as controls. After exposure to virus, tumor cells were washed twice and cultured at 37° C., 5% $CO_2$. Forty-eight h after transduction, media from each well was harvested and assayed for IL-2.

While no IL-2 was produced by any of these tumor cells prior to HSVil2 infection (Table 1), infection with HSVil2 resulted in IL-2 production by cells from all four of the tumors. In addition, as with the murine hepatoma cell lines, efficiency of gene expression was unaffected by irradiation with 10,000 rads. Finally, it is noteworthy that the entire procedure, including the radiation time, required less than 4 h, a time period that would be commensurate with intraoperative autologous vaccine generation, allowing potential reimplantation into exposed tumor sites during the same operative procedure.

EXAMPLE 4

Media and cell lysate from HSVil2-transduced tumor cells were harvested at 48 h and immediately frozen at −70° C. until assay. Immunoreactive IL-2 levels were determined by standard sandwich ELISA (Biosource International, Camarillo, Calif.). The total IL-2 produced in the forty-eight hours of cell culture were divided by two to arrive at average production per twenty-four hours. Interleukin-2 bioactivity in the supernatant or cell lysate was also determined by assessing their ability to induce proliferation of CTLL-2 cells in a standard cell mediated lympholysis (CML) assay (Zier, 1982). Briefly, $5\times10^5$ CTLL-2 cells were mixed with serial dilutions of test samples and cultured at 37° C., 5% $CO_2$. After 24 h, cell viability was measured by MTT (3-[4,5-dimethylthiazol-2-yl]-2,5-diphenyltetrazolium bromide; 5 mg/ml) incorporation. Recombinant human IL-2 (Chiron Corporation, Emeryville, Calif.) is used as an internal standard. Units are given as Cetus units.

EXAMPLE 5

To evaluation transduction efficiency, histochemical analysis was performed on tumor cells transduced with HSVlac. The cells were fixed at 48 h and histochemically stained with X-gal (Dannenberg & Suga, 1981). Briefly, plates containing transduced cells were fixed for 5 min with 1% glutaraldehyde, washed 3 times with PBS, then incubated with X-gal solution (X-gal (pH=7.4)[1 mg/ml] in PBS containing 2 mM $MgCl_2$, 5 mM $K_3Fe(CN)_6$, and 5 mM $K_4Fe(CN)_6$-$3H_2O$). Total cells and blue cells were counted and transduction efficiency expressed as percent of total cells that were blue.

EXAMPLE 6

To determine the in vivo effects of tumor vaccines produced using HSV-mediated gene transfer, syngeneic C57Bl/6j mice were immunized using murine HEPA 1–6 hepatoma cells radiated with 10,000 rads and then exposed to HSVil2 at an multiplicity of infection (MOI) of 1 for twenty minutes. The hepatoma cells ($10^6$ cells) were washed thrice with media after the twenty minute viral exposure and immediately injected either 1) subcutaneously, 2) intraperitoneally, or 3) intrasplenicly. Animals were given either a single injection or a daily injections on three consecutive days (three injections total). As controls, animals were injected with 1) media (media-control), or 2) a similar number of radiated tumor cells exposed to HSVlac (MOI=1), namely HSV carrying no cytokine genes (HSV-control). Animals were sacrificed three weeks later and splenocytes harvested for assessment of specific and non-specific tumor cell kill by coincubation with hepatoma for assessment of specific tumoricidal activity, K562 erythroblastic cell line for assessment of NK activity, or a syngeneic colorectal tumor cell line CO51 (ATCC; Rockville, Md.) for further assessment of non-specific tumoricidal activity.

In order to determine if vaccinations with HSV-modified tumor vaccine may alter in vivo response to tumor, C57Bl/6j mice were immunized by intrasplenic injection with 1) $10^6$ radiated tumor cells exposed to HSV carrying no cytokine genes (HSV-control), or 2) $10^6$ radiated, IL-2 secreting hepatoma cells. Three weeks later, the animals were injected intraportally with $10^6$ replicating hepatoma cells to determine host response to tumor. Three weeks after this tumor challenge, all animals were sacrificed, and tumor growth in the liver assessed.

Splenocyte isolation was carried out as follows. Spleens were harvested from pentobarbital anesthetized animals under sterile conditions. Each spleen was placed in a petri dish containing 10 ml of PBS, brought into the hood and transferred to a new petri dish with 10 ml of RPMI+10% FCS+50 µg/ml gentamicin. Splenocytes were washed from the spleen by repeated injection with media. Cells will be spun (300 g, 5 min) and resuspended in 5 ml of red blood cell lysis solution (pH=7.4) (0.15 M $NH_4Cl$, 1.0 mM $KHCO_3$, 0.1 mM $Na_2EDTA$). After 1 min, solution were diluted with 5 ml of RPMI, 10% FCS. Cells will be spun (300 g, 10 min) and washed 2× with media. Cells were then resuspended in 30 ml of RPMI+10% FCS+50 µg/ml gentamicin+30 U/ml IL-2 (Chiron Corp, Emeryville, Calif.) and kept in culture for 2 d prior to use. Prior to assay, cells were spun, resuspended, counted and volume adjusted to form the appropriate concentration.

Figure 3A:
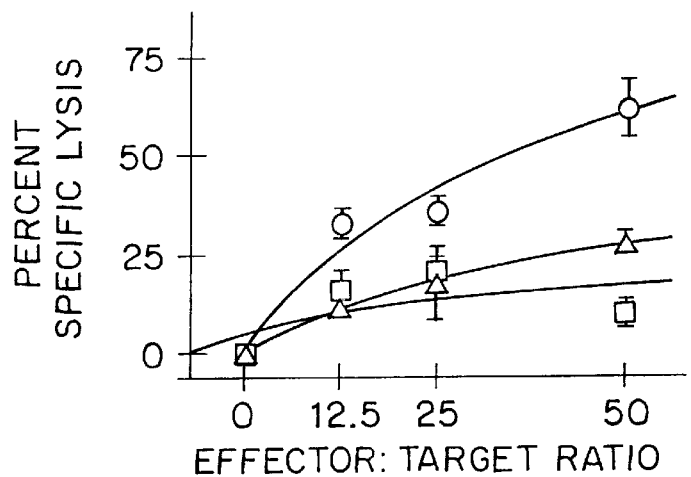
FIGS. 3A–C illustrate the tumoricidal activity splenocytes from mice treated by intrasplenic injection with HSV amplicon transduced tumor cells.
Figure 3B:
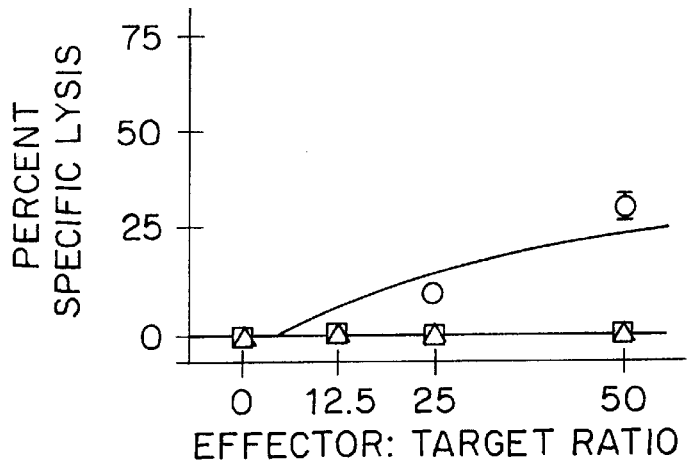
Figure 3C:
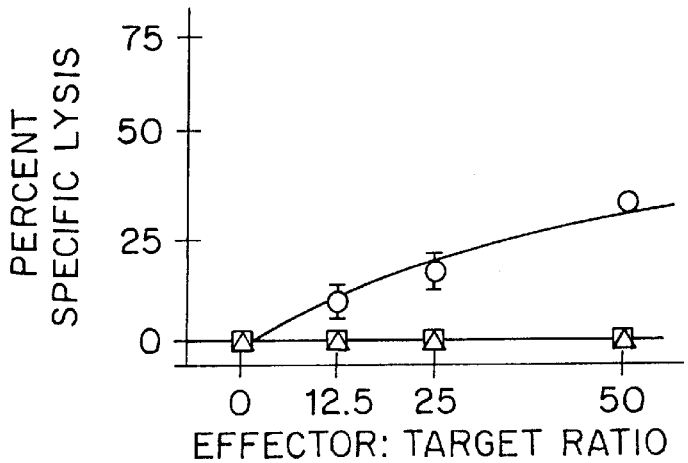

The experiments summarized above examining the effects of the route and number of injections on immunization, by the subcutaneous route or intraperitoneal route, showed that three injections were necessary for specific tumor immunity. However, for the intrasplenic route, the hepatoma cell line tested elicited specific immunity with a single injection (FIGS. 3A–C, FIG. 3A presents data for HEPA 1–6 targets; FIG. 3B for K562 targets and FIG. 3C for CO51 □=splenocytes from animals pretreated with irradiated tumor exposed to control media, Δ=splenocytes from animals pretreated with irradiated tumor exposed to HSV (HSV-control), ○=splenocytes from animals pretreated with irradiated tumor exposed to HSV-IL-2). This is the reason that the intrasplenic route was used for the subsequent experiment examining the effects of immunization on in vivo tumor growth.

Mice pretreated by intrasplenic injection of either 1) irradiated, HSV-treated tumor (HSV-control) or 2) irradiated, HSVil2 treated tumor were subsequently challenged with intraportal injection of $10^6$ replicating tumor cells to determine the effects of immunization on tumor growth. Immunization using irradiated IL-2 secreting tumor cells produced by HSV-mediated gene transfer conferred in vivo antitumor effects. In animals treated with HSV-control, seven of the ten animals challenged with $10^6$ hepatoma cells developed liver tumors, with mean tumor size being 1.5±0.4 gm (6±2% body weight). For animals pretreated with HSVil2 however, only one of ten animals developed tumor (p=0.02 vs HSV-control) with the size of that tumor being 0.2 gm (0.9% body weight).

EXAMPLE 7

K562 or tumor cells served as targets in in vitro europium release cytotoxicity assays. $5\times10^6$ cells from culture were washed 2× with Buffer 1 (pH=7.4) (50 mM Hepes, 93 mM NaCl, 5 mM KCl, 2 mM $MgCl_2$) then incubated in labeling solution (K562: 30 ml $EuCl_3$, 10 ml DTPA, 250 ml Dextran Sulfate in Buffer 1; Hep: 35 ml $EuCl_3$, 10 ml DTPA, 100 ml Dextran Sulfate in Buffer 1) for 15 min in an ice bath, mixing gently every 5 min. After 15 min, 20 ml of 100 mM $CaCl_2$ was added and the mixture incubated for 5 min. Nine ml of Repair Buffer (Buffer 1, 2 mM $CaCl_2$, 10 mM glucose) was added. Cells were spun (200 g, 10 min) and washed 4× with Repair Buffer and 3× with media. Cells then were resuspended and plated at a concentration of $5\times10^4$ cells/100 ml per well in a 96 well U-Bottom plate (Costar Corp., Cambridge, Mass.) containing effector cells in wells at effector to target ratios of 100:1, 50:1, 25:1, and 12.5:1. The plate was spun (10 g, 5 min), incubated (4–6 hr, 37° C.), and spun (100 g, 5 min). 20 µl of supernatant were transferred to a 96 well Flat Bottom plate (Costar Corp) already containing 180 µl Delfia Enhancement Solution (Wallac Oy, Turku, Finland). The plate was read in a 1232 Delfia Fluorometer (Wallac Oy). Maximum release was measure by lysing cells with 1% Triton X. Percentage specific lysis was equal to (experimental−spontaneous release)/(maximum release+spontaneous release)×100. Spontaneous release varied between 5 and 15% of max.

EXAMPLE 8

HSV vectors containing the gene for either IL-2 (HSVil2) or LacZ (HSVlac) were constructed in accordance with Example 1. Twenty-five Fischer rats with bilateral flank squamous cell lung tumors were randomized to receive left flank injections of either HSVil2, HSVlac, saline or no injection on weeks 5, 7 and 9 post-implantation. Tumor volume was measured 3 times weekly for 6 weeks. There were no significant differences in tumor growth and volume among the HSVlac, saline and non-injected groups. At 6 weeks, the HSVil2 group had an 81% reduction in mean tumor volume in the injected left flank compared to controls. There was also an 88% reduction in mean tumor volume in the opposite, non-injected flank, thus indicating that in vivo transfection of tumor by HSV vectors containing cytokine genes is effective to stimulate a systemic antitumor response. Four of the 5 HSVil2-treated animals were clinical responders. Staining studies for LacZ revealed transfection of tumor and surrounding stromal cells only on the treated side.

EXAMPLE 9

Murine GM-CSF, human IL-2 and LacZ genes were cloned directionally into HSVprPUC which contains the HSV immediate early 4/5 promoter, a multiple cloning site, and an SV40 A sequence, and packaged as previously described by Geller et al. (1990). RR1 cells (BHK cells stably transfected with the HSV IE3 gene) (20), along with D30 EBA helper virus (a strain 17-derived IE3 mutant deleted from codons 83 to 1236 and maintained in Dulbecco's modified Eagle medium (DME) containing high glucose [HG, 4.5 g/liter], 10% FCS, 1% penicillin/streptomycin, and 400 µg/ml of bioactive geneticin [G418; Gibco BRL, Gaithersburg, Md.] at 37° C. and 5% CO2) were used for packaging HSV arnplicons. To package amplicon vectors, $3 \times 10^6$ RR1 cells were plated in media containing 10% FCS and transfected 4 h later by adding 40 µl of Lipofectin (Gibco), waiting 5 min, and adding amplicon DNA solution dropwise (30 µg at 1 µg/µl in DME). 6 h later, plates were fed with media containing 5% FCS. 20 h after transfection, D30 EBA virus in 50–100 µl was added to achieve an moi of 0.2. 5 ml of complete media with 5% FCS were added to each plate after 1 h, and amplicon virus stocks were harvested 2 d later. After overnight storage at 70° C., fresh RR1 cells ($4 \times 10^6$ cells/60 mm plate) were infected with warmed (34° C.), sonicated virus stock. 2 d later, stocks were harvested and stored for subsequent use. HSVlac stocks were titered by an expression assay using NIH3T3 cells plated ($2 \times 10^5$ cells/well of a 24-well plate) and infected with increasing volumes of virus stock in duplicate. 24 h after infection, cells were fixed and stained with 5-bromo-4-chloro-3-indolyl-D-galactoside (X-gal) using standard methods. The number of X-gal+ (blue) cells were counted, and titers were expressed as the number of blue forming units/ml. The D30 EBA helper virus in each stock was titered by plaque assay on RR1 cells, and the cytokine-containing vectors were titered by slot blot analysis. For slot blot analysis, viral DNA was extracted twice from packaged virus by phenol/chloroform, ethanol-precipitated with single-strand calf thymus DNA as carrier, denatured at room temperature with 0.2 N NaOH, 0.5 M NaCl for 10 min, and loaded on a nylon membrane with a slot blot apparatus. The membrane was baked for 2 h at 65° C. and probed with a [32P]-labeled 435 bp SspI and PvuI fragment containing part of the β-lactamase gene from pBR322 (nucleotides 3733–4168). After stringent washing (0.1x SSC 2x for 15 min), blots were exposed to x-ray film, and various timed exposures taken and densitometrically scanned (LKB Ultroscan; Pharmacia LKB Biotechnology Inc., Piscataway, N.J.). Band densities and the titers of HSVil2 and HSV GM-CSF (expressed as particles/ml) calculated from the density relative to HSVlac given that this latter amplicon was titered by an expression assay, were compared. HSVlac titers were between $1-2 \times 10^6$ blue forming units/ml as titered by expression and X-gal biochemistry on NIH 3T3 cells. The HSVil2 and HSVGM-CSF titers were between $1-2 \times 10^6$ particles/ml. The ratio of D30 EBA helper virus to amplicon varied from 2:1 to 5:1. moi refers to the amplicon. Recombination for wild-type revertants was monitored by plaque assay on Vero cells and occurred at a frequency of $1 \times 10^6$.

To assess in vitro production of cytokines, $10^6$ hepatoma cells per 2 ml were plated in six-well plates (Costar), irradiated with 10,000 rad, and rested for 1 h. Cells were then exposed to HSV-IL12, HSVGM-CSF, HSVlac, or Media for 20 min at moi's of one and two and washed 2x with media. Cell culture supernatants were harvested on days 1, 2, 4, and 7 post-exposure, and cytokine levels were measured by ELISA (IL-2, R & D Systems, Minneapolis, Minn.; GM-CSF, Genzyme Corp., Cambridge, Mass.).

Figure 4A:
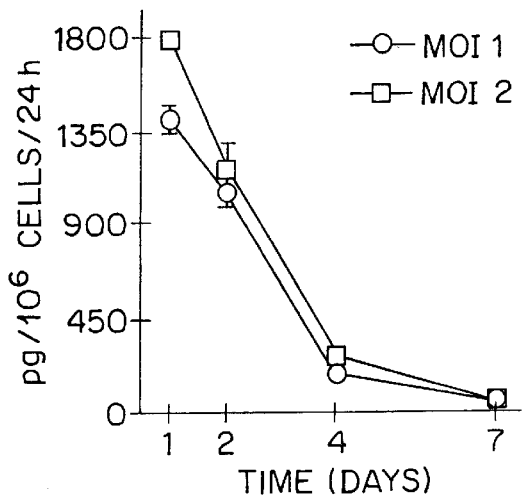
FIGS. 4A and 4B summarizes the results of studies on the efficiency of gene transfer using HSV amplicons according to the invention.
Figure 4B:
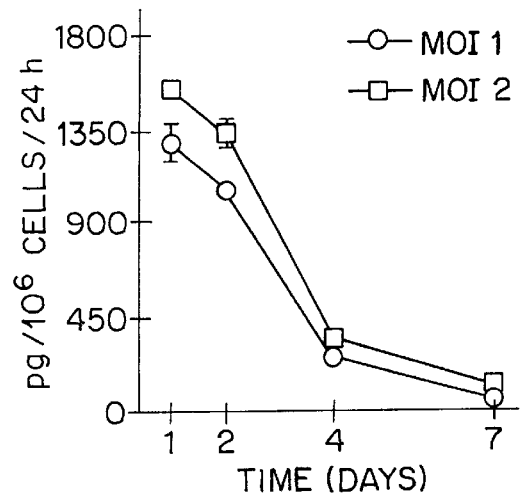

As shown in FIGS. 4A and 4B, control cells not exposed to cytokine gene-containing vectors do not produce cytokines, and no cytokines are seen immediately after transduction with HSVil2 and HSVgm-csf and washing, indicating that proteins are not injected along with the tumor cells. Cells exposed to HSVil2 or HSVgm-csf produce nanogram quantities of these cytokines per $10^6$ cells after vaccination, peaking on day 1 and decreasing thereafter.

EXAMPLE 10

Hepatoma cells in culture were irradiated with 10,000 rad, allowed to rest for 1 h, then exposed to HSVil2, HSVGM-CSF, HSVlac or media for 20 min at an moi of one. Cells were then washed 2x with media, and $10^6$ cells/200 µl were injected intrasplenically. An additional control group underwent injection of media alone. On day 18, half the animals in each group received either $5 \times 10^4$ U of γ-IFN i.p. or normal saline for 3 d. On day 21, all animals received a challenge of $5 \times 10^5$ hepatoma cells/200 µl intrasplenically followed by splenectomy 10 min later, allowing sufficient time for the hepatoma cells to migrate to the liver. Animals were killed 20 d later, and tumor nodules were counted. Additional animals were vaccinated, killed on d 2 and 18 post-vaccination, and heart, lung, liver, kidney and serum harvested for assessment of in vivo production of cytokines by ELISA.

Figure 5:
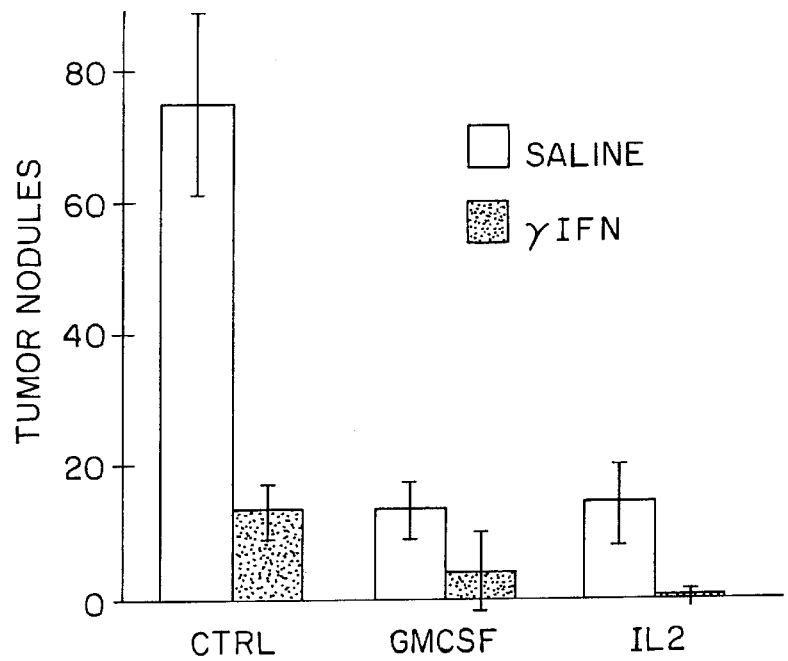
FIG. 5 illustrates the effect of transduced cells on tumor growth.

There was no significant effect on tumor growth as a result of vaccination with irradiated cells or vaccination with irradiated cells transduced with HSVlac compared to vaccination with medium alone. As shown in FIG. 5, animals immunized with IL-2 or GM-CSF-secreting cells or pretreated with γ-IFN had significantly fewer tumor nodules that all three control groups. Combination treatment with IL-2 or GM-CSF secreting cells and pretreatment with γ-IFN was more effective than any single treatment. Complete responses were seen in 8 of 11 IL-2 animals and 4 of 12 GM-CSF animals. No animal treated with γ-IFN alone was without tumor.

EXAMPLE 11

To assess the effects of vaccination on tumor growth following a partial hepatectomy (shown to be immunosuppressive and to accelerate the growth of hepatic tumors), animals were immunized intrasplenically with hepatoma vaccines (HSVil2, HSVGM-CSF, HSVlac) produced as above. On day 18, half the animals in each group received either $5 \times 10^4$ U of IFN intraperitoneally, or normal saline for 3 d. On day 21, all animals received a challenge of $5 \times 10^5$ hepatoma cells/200 µl intrasplenically followed by splenectomy 10 min later. Half the animals in each group underwent 70% partial hepatectomy 1 h after tumor injection. One control group did not undergo vaccination or partial hepatectomy. Animals were killed 18 d after tumor challenge, and nodules were counted. In previous experiments, the number of surface nodules was shown to correlate directly with tumor volume as measured by water displacement.

Figure 6:
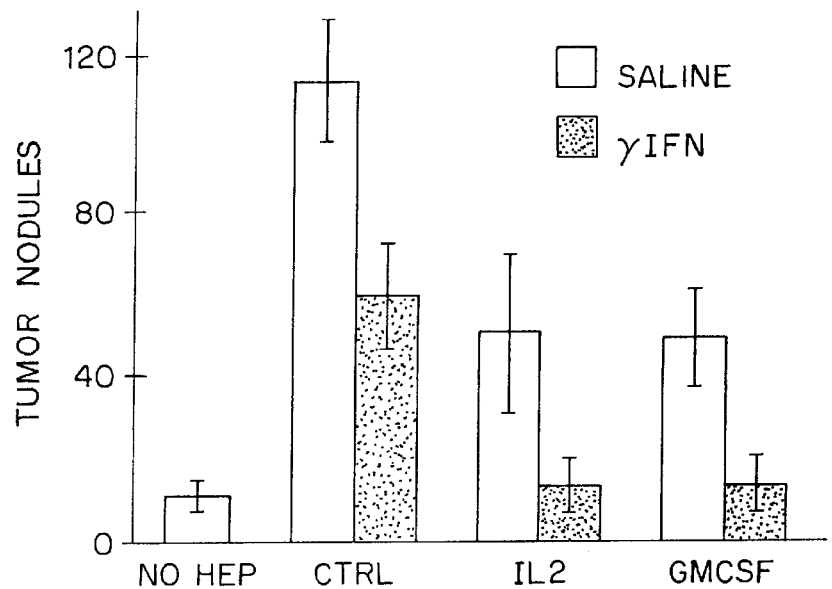
FIG. 6 illustrates the effects of transduced cells on hepatectomy induced tumor formation.

As shown in FIG. 6, treatment with IL-2 or GM-CSF secreting cell lines or pretreament with γ-IFN reduced the growth of hepatectomy-induced tumors. The best results, comparable to the results for animals with no hepatectomy, were obtained using a combination of either IL-2 or GM-CSF secreting cell lines and pretreatment with γ-IFN.

EXAMPLE 12

To assess the effect of vaccination and IFN on splenocyte and Kupfer cell (KC) function, animals underwent vaccination and IFN treatment as described in Example 11, and splenocytes and KC were harvested on day 21 postvaccination. Tumoricidal activity was assessed by mixing effectors with Europium-labeled tumor cells in an in vitro assay. Labeled cells were plated at a concentration of $5 \times 10^4$ cells/100 μl per well in a 96-well U-Bottom plate (Costar) containing effector cells in wells at varying effector to target ratios. The plate was spun (200 rpm, 5 min), incubated (4 h, 37° C.), and respun (500 rpm, 5 min). 20 μl of supernatant were transferred to a 96-well Flat Bottom plate (Costar) already containing 180 μl/well of Delfia Enhancement Solution (Wallac Oy, Turku, Finland). The plate was read in a 1232 Delfia Fluorometer (Wallac Oy). Maximum lysis was measured by lysing cells with 1% Triton X. Percent specific lysis is equal to experimental–spontaneous release/max. release+spontaneous release×100. Spontaneous release varied between 5 and 15% of max. Assays were performed in triplicate.

Vaccination with HSVlac or irradiated cells had no significant effect on either KC function or splenocyte activity. Splenocytes from animals vaccinated with HSVil2 or HSVgm-csf exhibited significantly greater killing of targets than splenocytes from control or γ-IFN-treated animals. γ-IFN did not appear to affect splenocyte activity. KC from rats pretreated with γ-IFN had significantly greater killing of targets than KC from controls. KC from rats vaccinated with HSVil2 also had significantly greater killing of targets than KC form controls, but not as great as KC from γ-IFN-treated rats. Vaccines secreting GM-CSF did not appear to affect KC activity.

EXAMPLE 13

Murine IL12m35, murine IL12m40, human IL2 and LacZ genes were cloned directionally into HSV/PRPuc and packaged as previously described. (Geller et al. (1990), Geller and Breakefield (1988), Federoff (1996). To produce HSVm75, the m35 and m40, genes were cloned directionally using appropriate restriction enzymes into HSV/PRPuc separated by an IRES fragment. HSVPrPUC contains the HSV immediate early 4/5 promoter, a multiple cloning site and SV40 A sequence. The RR1 cells used for packaging HSV amplicons were maintained in Dulbecco's modified Eagle's medium (DMEM) containing high glucose (HG, 4.5 g/l), 10% FCS, 1% penicillin/streptomycin and 400 μg/ml of bioactive geneticin (G418, Gibco) at 37° C., 5% $CO_2$. RR1 cells are BHK cells stably transfected with the HSV IE3 gene and were obtained from Dr. Paul Johnson. Johnson et al. (I1992). D30 EBA helper virus was prepared by growth on RR1 cells. D30EBA is a strain 17 derived 1E3 mutant deleted from codons 83 to 1236 and was obtained from Dr. Roger Everett. Paterson and Everett (1990). To package amplicon vectors, $3 \times 10^6$ RR1 cells were plated in media containing 10% FCS and 4 h later were transfected by adding 40 μl of Lipofectin (Gibco-BRL), waiting 5 min and then adding the amplicon DNA solution dropwise (30 μg at 1 μg/μl in DMEM). Six hours later, plates were fed with media containing 5% FCS. Approximately 20 h after transfection, D30 EBA virus in 50–100 μl was added to achieve a multiplicity of infection (MOI) of 0.2. Five ml of complete media with 5% FCS were added to each plate after 1 h. Amplicon virus stocks were harvested 2 days later. After overnight storage at −70° C., fresh RR1 cells ($4 \times 10^6$ cells/60 mim plate) were infected with sonicated and warmned (34° C.) virus stock. Two days later, the stocks were harvested and stored for subsequent use. HSVlac virus stocks were titered by an expression assay. In brief, NIH 3T3 cells were plated ($2 \times 10^5$ cells per well of 24 well plate) and infected with increasing volumes of an HSV amplicon virus stock in duplicate. Twenty-four h after infection, cells were fixed and stained with the chromogenic substrate 5-bromo-4-chloro-3-indolyl β-D-galactoside (X-gal) using standard methods. (Geller and Breakefield (1990)) The number of X-gal+ (blue) cells were counted. Titers are expressed as the number of blue forming units/ml. The D30 EBA helper virus in each stock was titered by plaque assay on RR1 cells, and HSVil2 was titered by a slot blot assay. For slot blot analysis, viral DNA was extracted from packaged virus by phenol/chloroform twice, ethanol precipitated with single strand calf thymus DNA as carrier, denatured at room temperature with 0.2 N NaOH, 0.5 M NaCl for ten minutes and loaded on nylon membrane with a slot blot apparatus. The membrane was then baked for 2 hours at 65° C., and probed with a [$^{32}$P]-labeled 435 bp Sspl and Pvul fragment containing part of the β-lactamase gene from pBR322 (nucleotides 3733–4168). After stringent washing (0.1× SSC twice for 15 minutes), blots were exposed to X-Ray film and various timed exposures taken and densitometrically scanned (LKB Ultroscan). Band densities between HSVlac and HSVil2 were compared and the titer of HSVil2 calculated from the density relative to HSVlac given that this latter amplicon was titered by an expression assay (blue forming units on NIH 3T3 cells). The titers of HSVil2 are expressed as particles/ml.

HSVlac titers were between $2 \times 10^6$ blue forming units/ml as titered by expression and X-gal histochemistry on NIH 3T3 cells. The HSVil2 titers, determined by slot blot (described above), were between 0.8 and $2 \times 10^6$ particles/ml. D30EBA titers in stocks ranged between $5 \times 10^6$ to $6 \times 10^7$ plaque forming units/ml. Recombination for wildtype revertants was monitored by plaque assay on Vero cells and occurred at a frequency of $1 \times 10^{-6}$.

EXAMPLE 14

Efficiency of transduction with HSVm35+HSVm40 vs. HSVm75 was assessed by measuring in vitro production of cytokines. To assess in vitro production of cytokines, $10^6$ hepatoma cells per 2 ml were plated in 6-well plates (Costar), radiated with 10,000 rads and rested for 1 h. Cells were than exposed to HSVm35, HSVm40, HSVm35+HSVm40, HSVm75, HSVlac or Media for 20 min at a multiplicity of infection (MOI) of between 1 and 4 and then washed 2× with media. Cell culture supernatants were harvested on days 1, 2, 4, 5 and 7 postexposure, and cytokine levels were measured by ELISA specific for the heterodimeric protein.

Control cells not exposed to cytokine gene-containing vectors do not produce cytokines. IL12 production was not detected in cells transduced with either HSVm35 or HSVm40 alone. Transduction using 2 vectors produced levels of IL12 similar to transduction using a single vector carrying both genes, which peak on day 1 and decrease thereafter

EXAMPLE 15

To determine the effect of vaccination on hepatic tumor growth, hepatoma cells in culture were radiated with 10000 rads, rested for 1 h, then exposed to HSVil2, HSVm75, HSVil2+HSVm75, HSVm35+HSVm40, or media for 20 min at an MOI of 1–4. Cells were washed 2× with media, and $10^6$ cells/200 µl were injected intrasplenically. An additional group received 2 populations of cells: $10^6$ HSVil2-transduced cells and $10^6$ HSVm75-transduced cells. On day 21, all animals received a challenge of $5\times10^5$ hepatoma cells/200 µl intrasplenically followed by splenectomy 10 min later. This model produces uniform numbers of tumors within the liver that can be counter on day 20 after tumor challenge. Operative procedures were performed under pentobarbital anesthesia (25 mg/kg i.p.) via midline abdominal incision. Animals were sacrificed 20 days later and tumor nodules counted.

Animals immunized with cells transduced by HSVm35+ HSVm40, HSVm75 or HSVil2 had significantly fewer tumor nodules than control. Vaccination with 2 tumor cell populations, one secreting IL2 and one secreting IL12, was more effective than vaccination with a single population of cytokine-secreting cells. Vaccination with a single population of cells transduced by both HSVil2 and HSVm75 was the most effective treatment, significantly better than any single treatment or two population treatment.

EXAMPLE 16

To access the effect of vaccination on splenocyte and KC Function, animals underwent vaccination as described in Example 15, and splenocytes and KC were harvested on day 21 post-vaccination and assessed for tumoricidal activity by standard Europium-release assay. Briefly, tumoricidal activity was assessed by mixing effectors with Europium-labeled tumor cells in vitro. Labeled cells were plated at a concentration of $5\times10^4$ cells/100 µl per well in a 96 well U-Bottom plate (Costar) containing effector cells in wells at varying effector to target ratios. The plate was spun (200 rpm, 5 min), incubated (4 hr, 37° C.), and spun (500 rpm, 5 min). 20 µl of supernatant were transferred to a 96 well Flat Bottom plate (Costar Corp) already containing 180 µl/well of Delfia Enhancement Solution (Wallac Oy, Turku, Finland). The plate was read in a 1232 Delfia Fluorometer (Wallac Oy). Maximum lysis was measured by lysing cells with 1% Triton X-100. Percent specific lysis is equal to (experimental−spontaneous release)/(max. release+ spontaneous release)×100. Spontaneous release varied between 5 and 15% of max. Assays were performed in triplicate.

Splenocytes from animals vaccinated by either HSVil2 or HSVm75 had significantly greater killing of targets than splenocytes from animals vaccinated by radiated cells. Splenocytes from animals vaccinated by cells transduced by HSVm75 and HSVil2 had significantly greater killing of targets than splenocytes from animals vaccinated by a single cytokine at an effector to target ratio of 100:1.

KC from rats vaccinated with HSVil2 or HSVm75 had significantly greater tumoricidal activity than KC from controls (p<0.05) at effector to target ratio of 50:1. KC from animals vaccinated by cells transduced by HSVm75 and HSVil2 had significantly greater killing of targets than KC from animals vaccinated by a single cytokine at an effector to target ratio of 100:1.

EXAMPLE 17

Human ICAM-1 and E. coli β-galactosidase cDNA was directionally cloned into HSVPrPuc (HSVhicam1 and HSV-lac respectively) which contains the HSV immediate early 4/5 promoter, a multiple cloning site, and an SV40 A sequence, and packaged as previously described in Example 1. RR1 cells (BHK cells stably transfected with the HSV IE3 gene), along with D30 EBA helper virus (a strain 17-derived IE3 mutant deleted from codons 83 to 1236 and maintained in Dulbecco's modified Eagle medium (DME) containing high glucose [HG, 4.5 g/liter], 10% FCS, 1% penicillin/ streptomycin, and 400 µg/ml of bioactive geneticin [G418: Gibco BRL, Gaithersburg, Md.] at 37° C. and 5% CO2) were used for packaging HSV amplicons.

To package amplicon vectors, $3\times10^6$ RR1 cells were plated in media containing 10% FCS and transfected 4 hours later by adding 40 µl of Lipofectin (Gibco), waiting 5 min, and adding amplicon DNA solution dropwise (30 µg at 1 µg/µl in DME). Six hours later, plates were fed with media containing 5% FCS. Twenty hours after transfection, D30 EBA virus in 50–100 µl was added to achieve a multiplicity of infection (MOI) of 0.2. Five ml of complete media with 5% FCS were added to each plate after 1 hours, and amplicon virus stocks were harvested 2 days later. After overnight storage at 70° C., fresh RR1 cells ($4\times10^6$ cells/60 mm plate) were infected with warmed (34° C.), sonicated virus stock. Two days later, stocks were harvested and stored for subsequent use. HSVlac stocks were titered by an expression assay using NIH3T3 cells plated ($2\times10^5$ cells/ well of a 24-well plate) and infected with increasing volumes of virus stock in duplicate. Twenty four hours after infection, cells were fixed and stained with 5-bromo-4-chlor-3-indolyl Beta-D-galactosidase (X-gal) using standard methods. The number of X-gal+ (blue) cells were counted, and titers were expressed as the number of blue forming units/ml.

The D30 EBA helper virus in each stock was titered by plaque assay on RR1 cells, and the cytokine-containing vectors were titered by slot blot analysis. For slot blot analysis, viral DNA was extracted twice from packaged virus by phenol/chloroform, ethanol-precipitated with single-strand calf thymus DNA as carrier, denatured at room temperature with 0.2 N NaOH, 0.5 M NaCl for 10 minutes, and loaded on a nylon membrane with a slot blot apparatus. The membrane was backed for 2 hours at 64° C. and probed with a [32p]-labeled 435 bp SspI and PvuI fragment containing part of the Beta-lactamase gene from pBR322 (nucleotides 3733–4168). After stringent washing (0.1× SSC 2× for 15 min), blots were exposed to x-ray film, and various timed exposures taken and densitometrically scanned (LKB Ultroscan: Pharmacia LKB Biotechnology Inc., Piscataway, N.J.). Band densities and the titers of HSVhicam1 (expressed as particles/ml) calculated from the density relative to HSVlac given that this latter amplicon was titered by an expression assay, were compared. HSVlac titers were between 1–$2\times10^6$ blue forming units/ml as titered by expression and X-gal biochemistry on NIH3T3 cells. The HSVhicam1 titers were between 1–$2\times10^6$ particles/ml. The ratio of D30 EBA helper virus to amplicon varied from 2:1 to 5:1. MOI refers to the amplicon. Recombination for wild-type revertants was monitored by plaque assay on Vero cells and occurred at a frequency of $1\times10^{-6}$.

EXAMPLE 18

The tumor cell line Morris Hepatoma McA-RH7777 (ATCC CRL 1601) was maintained in culture (DME, 6.25%

FCS, 20% Horse serum, 2 mM L-Glutamine) and periodically implanted into buffalo rat flanks to ensure tumorigenicity. This cell line was tested to be free of mycoplasma and viral infection.

Hepatoma cells from culture were radiated with 10,000 rads and rested for 1 hour. Cells were then exposed to HSVhicam1, HSVlac or nothing at an MOI of 1 for 20 minutes at 37° C. Cells were then washed with media twice and maintained in culture until analysis. To assess the cell surface expression of hICAM1, cells were harvested at 1, 2, 5 and 7 days after transduction and washed twice with HBSS containing 10 mM HEPES. Separate aliquots of cells were then incubated on ice for 20 minutes with anti-human ICAM-1 (Clone MEM 111, Caltag, Burlingame, Calif.) and anti-rat ICAM-1 (Clone 1A29, Caltag, Burlingame, Calif.) antibodies conjugated to PE or FITC. Additional aliquots of cells were incubated with isotype controls (Caltag, Burlingame, Calif.) to account for nonspecific binding of antibodies. Cells were then analyzed with a FACscanner (Becton Dickinson) for the presence of human and rat ICAM.

With PE labeling, greater than 90% of normal untreated rat hepatoma cells expressed rat ICAM on the cell surface with mean fluorescent intensities ranging from 200 to 288. There was no difference in rat ICAM expression between transduced and non transduced cells. Cells transduced with HSVlac or nothing had no detectable surface human ICAM-1. Flow cytometric analysis of rat hepatoma cells transduced with HSVhicam1 showed that a 20 minute exposure, at an MOI=1 resulted in high level expression of human ICAM on the surface of tumor cells. Peak cell surface positivity for human ICAM-1 was found 24 hours after transduction and tapered off by 1 week (Percent of cells positive for hICAM1 was 25%, 16%, and 9% on days 1, 2 and 5 post transduction). Mean fluorescent intensity of human ICAM-1 on HSVhicam1-transduced cells was 450, 271, and 124 on days 1, 2 and 5 respectively. On day 7 post transduction with HSVhicam1, cell viability was limited, but approximately 4% of viable cells were positive for surface hICAM1.

Figure 7:
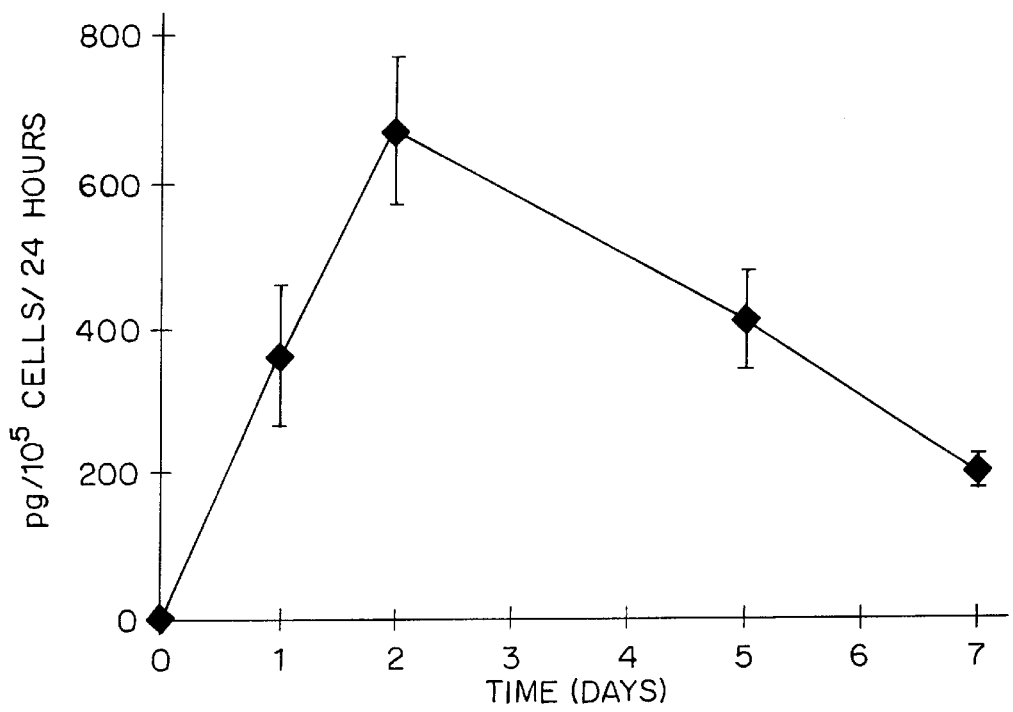
FIG. 7 shows the amount of human ICAM-1 found in cell culture supernatants for transduced cells.

FIG. 7 illustrates the quantitation of soluble human ICAM found in cell culture supernatants of transduced cells. No soluble human ICAM was detectable in supernatants of cells transduced with HSVlac or nothing. Levels in supernatants of transduced cells peaked at 48 hours after transduction and approached the level of detection by day 7.

EXAMPLE 19

To determine if ICAM-1 transduced hepatoma cells bound lymphocytes more avidly, a modification of previously reported adhesion assays (Miki, et al., 1993) was performed. Briefly, hepatoma cells were radiated with 10,000 rads, exposed to HSVhicam1, HSVlac or nothing for 20 minutes at 37° C. and washed with media twice. Cells were then plated in nearly confluent monolayers in 96 well plates. Splenocytes were harvested from normal Buffalo rats one day prior to each assay and cultured overnight in Complete RPMI (0.01 mM NEAA, 1 mM NaPyruvate, 2 mM L-Glutamine, 50 $\mu$M 2-ME, Pen/Step) containing 10% FCS, 50 U/ml IL2 (Chiron Corporation, Emeryville, Calif.), 5 $\mu$g/ml Con A (Sigma, St. Louis, Mo.), and 50 $\eta$g/ml PMA (Phorbol 12-Myristate 13-Acetate) (Sigma, St. Louis, Mo.). On the day of the assay, nonadherent splenocytes were harvested at a concentration of $10^6$/cc, and labeled with MTT (5 mg/ml PBS) in a v:v ratio of 3:1 (splenocytes:MTT). Splenocytes were incubated with MTT for 6 hours at 37° C. with gentle agitation every 30 minutes. Labeled lymphocytes were then plated at a concentration of $10^6$/100 $\mu$l in the wells containing the hepatoma targets. The cells were then co-incubated at 37° C. for 30 minutes. Nonadherent splenocytes were then gently washed off with PBS. Adherent lymphocytes were lysed with DMSO and read by spectrophotometry at 570 $\eta$m. Representative wells were used to count the number of hepatoma targets present for each experimental group. Additional labeled splenocytes were plated at varying concentrations, lysed and read by spectrophotometry in order to create a standard curve for the number of splenocytes per well. An adhesion index calculated as the number of adherent lymphocytes per hepatoma target cell and the mean of 8 wells was recorded.

Figure 8:
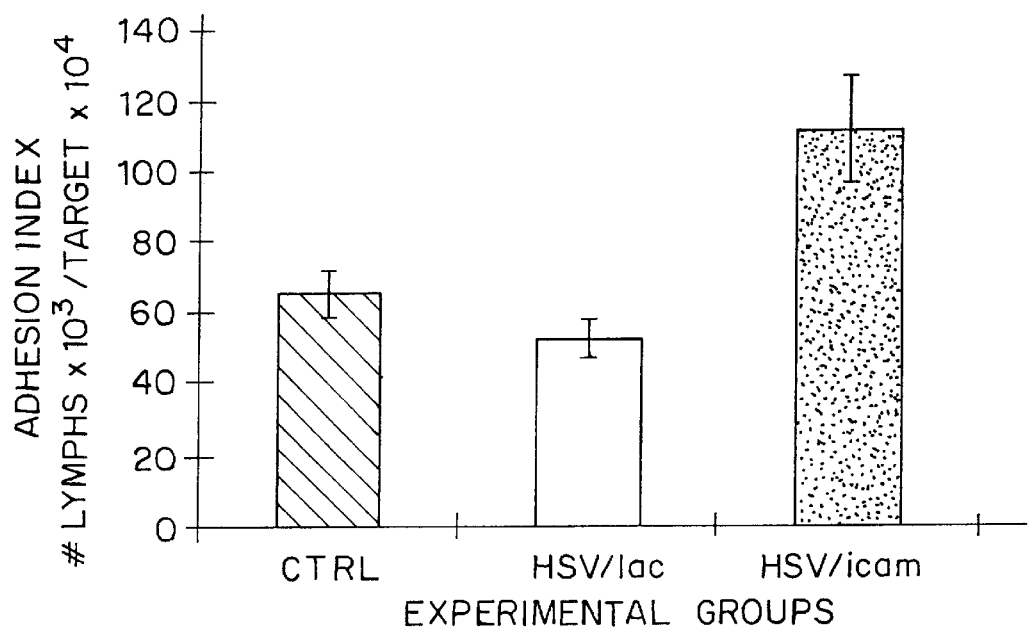
FIG. 8 shows the adhesion index for adhesion of lymphocytes to hepatoma cells transduced with HSVhICAM1 versus controls.

In order to determine if hICAM1 gene transfer would alter lymphocyte binding by tumor, an in vitro lymphocyte binding assay was used. There was a significant increase in the number of adherent lymphocytes per hepatoma target cell in wells containing HSVhicam1-transduced cells compared to lac-transduced and untreated cell (FIG. 8). This doubling of lymphocyte binding was statistically significant ($p<0.05$).

EXAMPLE 20

In order to determine if transduction of hepatoma cells with the ICAM-1 gene altered in vitro growth properties, cell proliferation assays were performed. Replicating rat hepatoma cells were exposed to HSVhicam1, HSVlac or nothing at an MOI of 1 for 20 minutes at 37° C. Cells were then plated in 24 well plates at a concentration of $10^4$ viable cells/ml/well. Cells were harvested by trypsin disaggregation at 1, 2 and 4 days after plating and counted by trypan blue exclusion. The mean count of 8 wells per time point was compared. Cells transduced with HSVhicam1 grew similarly in culture compared to HSVlac-transduced cells and untreated cells, indicating that changes in in vivo tumor growth (see example 21) cannot be accounted for by changes in intrinsic growth rate of the modified tumor.

EXAMPLE 21

Male Buffalo rats (Harlan Sprague Dawley) were housed 2 per cage in a temperature (22° C.) and humidity controlled environment and were given water and standard rat chow (PMI Mills, St. Louis, Mo.) ad libitum. They were maintained in 12 hour light/dark cycles. All surgical procedures were carried out through a midline laparotomy under i.p. pentobarbital (50 mg/kg) anesthesia. For major abdominal operations, 3 ml of 0.9% saline was administered i.p. for resuscitation post operatively. All animals received care under approved protocols in compliance with Memorial Sloan-Kettering Cancer Centers Institutional Animal Care and Use Committee guidelines.

Tumorigenicity Experiments

In order to analyze the effects of ICAM-1 overexpression on the in vivo growth characteristics of hepatoma cells, flank tumorigenicity experiments were performed. Animals (n=5 per group) were randomized to receive subcutaneous left flank injections of $10^6$ viable rat hepatoma cells transduced with HSVhicam1, HSVlac or nothing (MOI of 1). On the opposite right flank, all animals received subcutaneous flank injections of $10^6$ viable non-transduced cells. Animals were weighed and tumors measured with external calipers twice weekly. Tumor measurements were made in two perpendicular dimensions and averaged. Tumor volume was calculated using the equation $4/3\pi r^3$.

Figure 9:
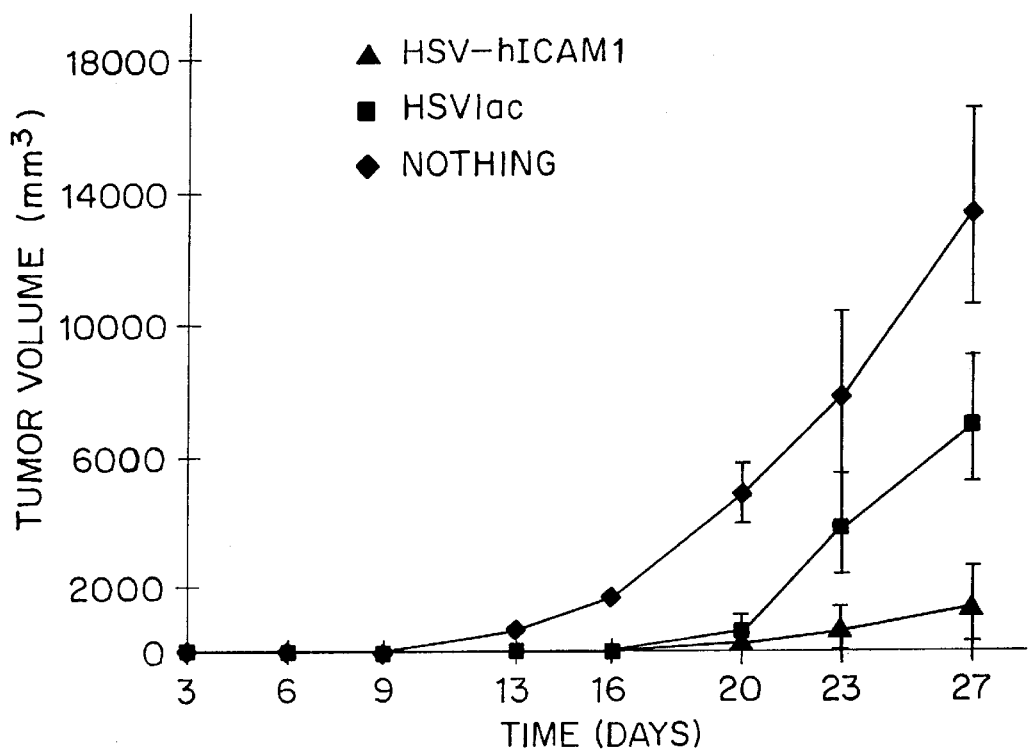
FIG. 9 shows tumor growth in rats injected with hepatoma cells transduced with HSV-hICAM1 versus controls.

There was significantly decreased tumor growth in the left flanks of animals injected with HSVhicam1-transduced cells compared to controls (FIG. 9). Tumor volumes at the termination of the experiment were compared. Tumors transduced with HSVhicam1 had a significantly (p<0.05) smaller volume (1,397+/−1296 mm$^3$) compared to tumors transduced with HSVlac (7,109+/−2118 mm$^3$) and untreated tumors (13,556+/−3354 mm3). On the contralateral untreated side, all groups had progressive tumor growth that was not significantly different.

Immunohistochemistry

In order to assess potential immunologic mechanisms of tumor regression, Immunohistochemical analysis of cell infiltrates in tumors was carried out. Animals from additional tumorigenicity experiments had tumors excised at 1 week and 3 weeks after injection of cells (n=5 per time point) and placed immediately in 10% buffered formalin. Twenty four hours later, tumors were embedded in paraffin using standard techniques. Five μm sections were made. Hematoxylin and Eosin staining was performed using standard techniques. The following antibodies were used for immunohistochemical analysis; mouse monoclonal anti-rat CD4 (IgG$_1$, clone W3/25, Serotec, Oxford, England), mouse monoclonal anti-rat CD8 (IgG$_1$, clone OX-8, Caltag, Burlingame, Calif.), and mouse monoclonal anti-rat 1-A (IgG$_1$, clone OX-6, Serotec, Oxford, England) which recognizes rat MHC Class II. The secondary antibody used was Biotinylated anti-mouse IgG, rat adsorbed (Vector, Burlingame, Calif.). Slides used for CD4 and CD8 staining were pretreated with lmM EDTA (ph 8) in a microwave for 10 minutes. For MHC II staining, slides were pretreated for 10 minutes with a 0.05% Protease XXIV (Sigma, St. Louis, Mo.) in Tris-HCI buffer, ph 7.6. Endogenous peroxidase was then quenched with a five minute incubation in 3% H$_2$O$_2$. After washes with PBS, slides are then placed in 0.05% bovine serum albumin for 1 minute. Slides were then dried and whole horse serum applied at a 1:20 dilution in 2% bovine serum albumin and incubated for 10 minutes. Serum was then suctioned off and 150 μl of primary antibody applied. The primary antibody was incubated for 16 −18 hours at 4° C. in a humidity chamber. After PBS washes, secondary antibody was applied to the slides at a 1:500 dilution in 1% bovine serum albumin and incubated for 60 minutes at room temperature in a humidity chamber. Slides were then washed in PBS and peroxidase-conjugated streptavidin was applied at a dilution of 1:500 in 1% bovine serum albumin. Slides were then washed with PBS and transferred to a bath of 0.06% diaminobenzidine (Sigma, St. Louis, Mo.) for 5 to 15 minutes. Slides were then washed in water and decolorized with 1% acid alcohol and blue in ammonia water. Dehydration with ethanol and xylene were carried out with standard techniques and slides were mounted with Permount (Fisher, Pittsburgh, Pa.) mounting media.

A single pathologist blinded to the experiment reviewed slides and graded them in the following way. Tumor cells were assessed for the presence or absence of MHC II staining. The degree of tumor infiltration with MHC II staining non-tumor cells was graded from 1 to 4. The degree of infiltration of tumors with the total amount of CD4 and CD8 positive lymphocytes was graded from 1 to 4. The relative percentage of CD4 and CD8 positive cells was then assessed and expressed as a ratio. Rat splenic tissue was used as a positive control for each experiment.

The amount of infiltration of tumors with both CD4 and CD8 positive T lymphocytes did not differ between treatment groups at 1 and 3 weeks. The ratio of CD4 to total CD4 and CD8 positive T cells did not differ between groups at 1 week, but at 3 weeks, there was a significant increase in this ratio in the HSVhicam1-treated animals compared to HSV-lac and untreated animals (0.42 vs. 0.25 and 0.24, p<0.05). There was no significant difference in the degree of infiltration of tumors with MHC II staining immune cells between treatment groups at 1 and 3 weeks. Tumor cells did not stain positively for MHC II expression in any case.

EXAMPLE 22

In order to determine whether previous exposure to ICAM-1 transduced hepatoma cells would protect against future challenges with the parental tumor, vaccination experiments were performed. Whole tumor cell vaccines were prepared as follows. Rat hepatoma cells were radiated with 10,000 rads, exposed to HSVhICAM1, HSVlac or nothing at an MOI of 1 for 20 minutes at 37° C. and washed twice with media. Animals (n=19 per group) were then randomized to receive either cell type by intrasplenic injections of 10$^6$ cells in 200 μl of media on day 1. Control animals received 200 μl of media intrasplenically. Three weeks after vaccination, animals were challenged with 5×10$^5$ replicating hepatoma cells by intrasplenic injection. After 10 minutes, a splenectomy was performed in all animals. Three weeks after challenge, animals were sacrificed and liver surface tumor nodules counted. Body weights were recorded and grooming habits monitored twice a week throughout the experiment.

Figure 10:
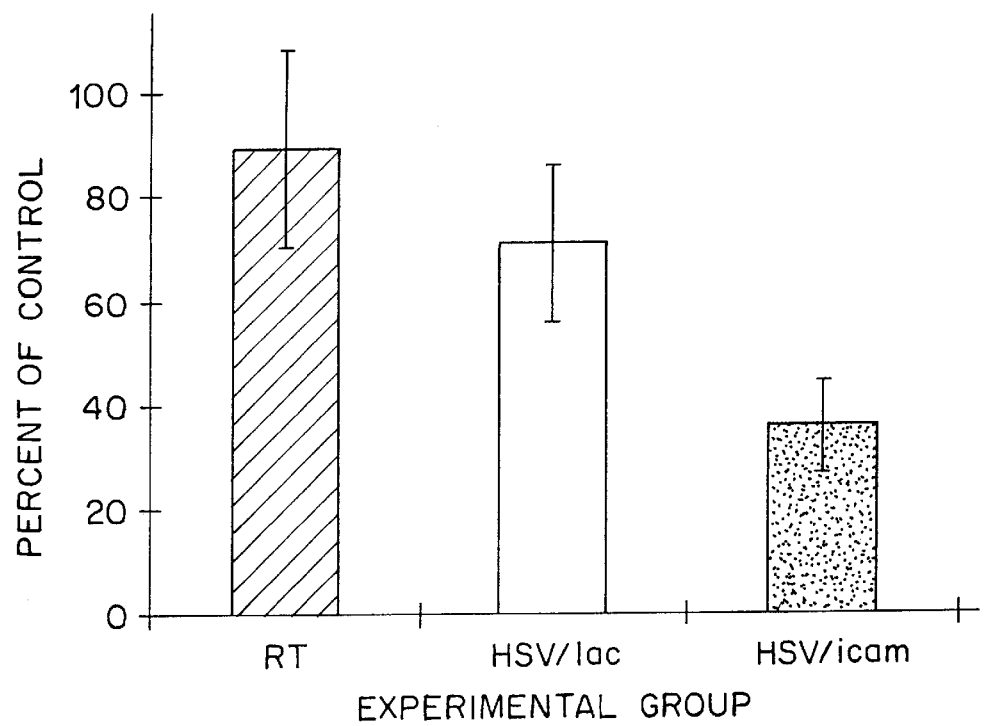
FIG. 10 shows tumor nodules formed in rat liver after vaccination with radiated (nonviable) HSVhICAM1-transduced hepatoma cells followed by challenge with viable hepatoma cells.

Throughout the experiment, there was no difference in weight gain in all treatment groups and all animals maintained normal grooming habits. As illustrated in FIG. 10, there was significantly decreased uptake and growth of hepatic metastases in animals vaccinated with HSVhicam1 cells compared to all controls (p<0.05). There was no difference between animals vaccinated with HSVlac-transduced cells, radiated cells alone or media.

EXAMPLE 22

The coding sequences for human B7.1 or human RANTES were cloned into the polylinker region of the pHSVPrPUC plasmid. To form the HSV-B7.1 amplicon, pBJ.huB7.1 plasmid (kindly provided by Dr. Lewis Lanier, DNAX, Palo Alto, Calif.) was digested with HindIII and was filled in to generate a blunt end and. Subsequently, this plasmid was digested with Xbal. A The HindIII blunt/Xbal fragment encoding the for the human B7.1 cDNA was gel purified and used as insert in the ligation with the vector. The HSV amplicon vector pHSVPrPUC plasmid was digested with EcoRI and filled in with Klenow to make a blunt end, followed by Xbal digestion. The EcoRIblunt/Xbal vector fragment was gel purified and ligated with the insert. The constructed amplicon plasmid was analyzed for the orientation of the coding sequences of huB7.1 with respect to the HSV-1 IE4/5 promoter, and the amplicon used in the generation of the HSVB7.1 amplicon virus.

Figure 11:
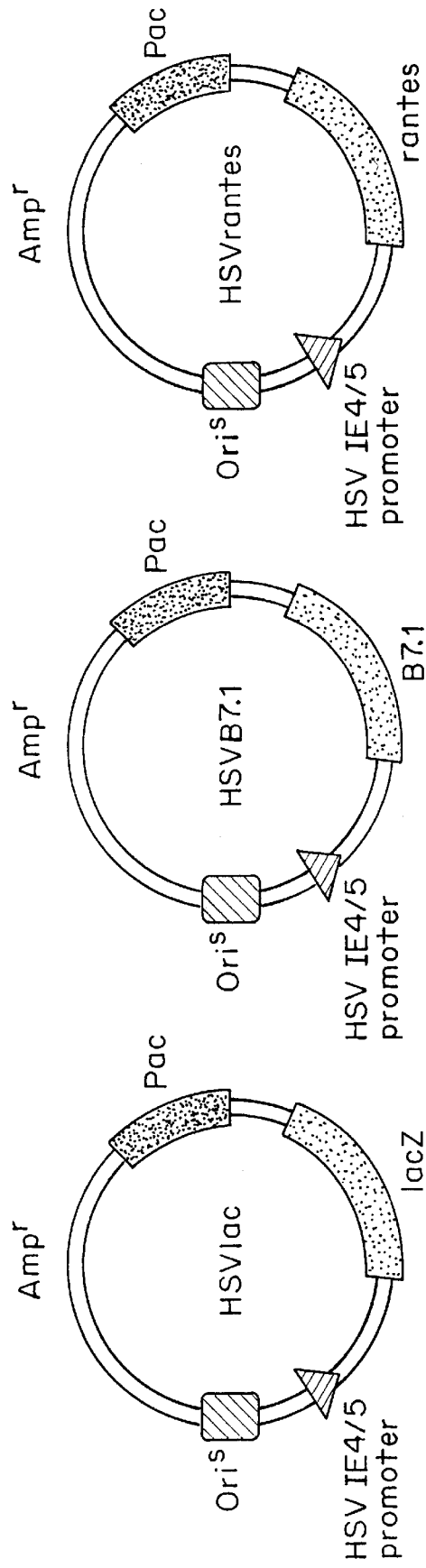
FIG. 11 shows the structure of several HSV-immunomodulatory protein amplicons in accordance with the invention.

To form the HSV-RANTES amplicon, SK+pBS-RANTES plasmid (kindly provided by Dr. Tom Schall, ChemoCentryx, MountainView, Calif.) was partially digested with Kpnl followed by digestion with Xbal. The Kpnl/Xbal fragment encoding human RANTES cDNA was gel purified and used as insert in the ligated to the HSV amplicon vector pHSVPrPUC plasmid digested with Kpnl and Xbal. Orientation of the coding sequences for huRANTES with respect to the HSV-1 IE4/5 promoter was verified, and the amplicon used in the generation of the HSVrantes amplicon virus. The HSV amplicons are shown schematically in FIG. 11.

EXAMPLE 23

Amplicon DNA was packaged into HSV-1 particles by transfecting 5 μg of plasmid DNA into RR1 cells with lipofectamine as recommended by the manufacturer (GIBCO-BRL). Following incubation for 24 hours the transfected monolayer was superinfected with the HSV strain 17, IE3 deletion mutant virus D30EBA (Paterson et al., 1990) at a multiplicity of infection (MOI) of 0.2. Once cytopathic changes were observed in the infected monolayer, the cells were harvested, freeze-thawed, and sonicated using a cup sonicator (Misonix, Inc.). Viral supernatants were clarified by centrifugation at 5000 g for 10 min prior to repeat passage on RR1 cells. This second viral passage was harvested as above and concentrated overnight by ultracentrifugation in a 25% sucrose gradient as previously described (Tung et al., 1996). Viral pellets were resuspended in PBS (Ca2+ and Mg2+ free) and stored at −80° C. for future use. Stocks were titered for helper virus by standard plaque assay methods. Amplicon titers were determined as follows: NIH 3T3 cells were plated in a 24-well plate at a density of $1 \times 10^5$ cells/well and infected with the virus. Twenty-four hours after viral infection the monolayers.were washed twice in PBS and either fixed with 4% paraformaldehyde and stained by X-gal histochemistry (5 mM Potassium Ferricyanide; 5 mM Potassium Ferrocyanide; 0.02% NP-40; 0.01% sodium deoxycholic acid; 2 mM $MgCl_2$ and 1 mg/ml Xgal dissolved in PBS) or harvested for total DNA using lysis buffer (100 mM NaCl, 10 mM Tris, pH 8.0, 25 mM EDTA, 0.5% SDS) followed by subsequent phenol/chloroform extraction and ethanol precipitation. PCR was performed on duplicate samples using primers corresponding to the β-lactamase gene present in the amplicon plasmid under the following conditions: 94° C., 2 min; then 20, 23 or 26 cycles of 94° C. (30 sec), 58° C. (30 sec), followed by 72° C. (7 min). PCR products from early and late cycles were run on a 1% ethidium bromide gel, and the 450 bp band intensities were assessed using the FOTDODYNE FOTO/ECLIPSE™ system (Fotodyne, Inc, Hartland, Wis.) and COLLAGE™ Image Analysis Software. HSVB7.1 and HSVrantes titers were estimated by comparison with HSVlac virus as standards. Plaque forming unit (pfu/ml) and amplicon (bfu/ml) titers obtained from these measurements were used to calculate amplicon titer and thus standardize experimental viral delivery. Amplicon titer in the different virus preparations ranged from $1-10 \times 10^7$ bfu/ml and the helper titers were in the range of $5-15 \times 10^7$ pfu/ml.

EXAMPLE 24

EL4 cells were infected in vitro either with HSVB7.1, or HSVlac amplicon virus at an MOI of 0.5–1–5 pfu per cell. Specifically, $10^6$ EL4 cells were adsorbed with the amplicon virus in a volume of 0.5 ml at 37° C., 5% $CO_2$ for 4 hours. At the end of 4 hours, 0.5 ml of fresh ID-10 medium was added and incubation continued for another 12 hours. The infected cells were harvested at the end of 16 hours and $10^6$ cells in 0.1 ml of chilled PBS were stained with 1:10 diluted phycoerythrin (PE) conjugated anti-B7.1 antibody (anti-CD80 PE, Becton-Dickinson) for 30 minutes at 4° C. Uninfected EL4 cells (as negative control), or EL4 stably expressing B7.1 (EL4-B7.1 as cells as positive control) were also stained simultaneously with the anti-CD80 PE antibody. The stained cells were analyzed by flow cytometry using an EPICS flow cytometry instrument.

Figure 12A:
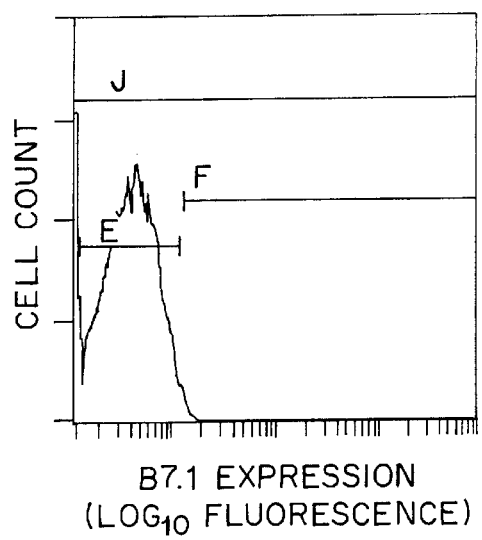
FIGS. 12A–C show B7.1 expression in EL4 cells transduced with HSVB7.1 versus controls.
Figure 12B:
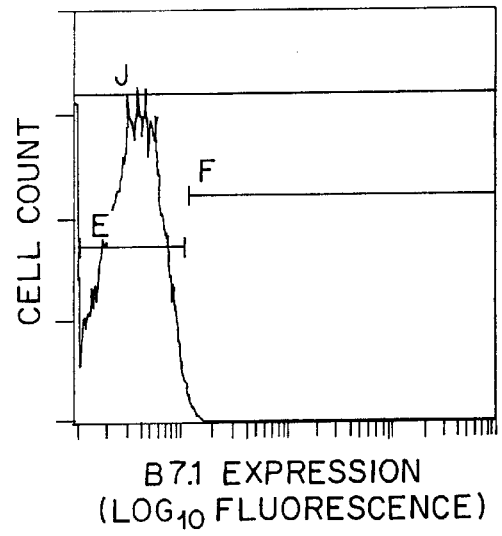
Figure 12C:
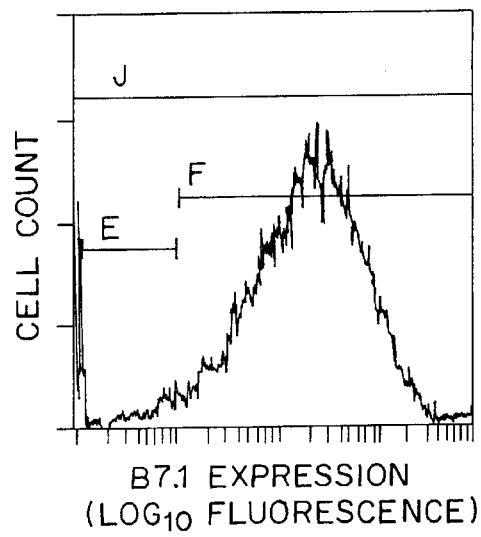

Control uninfected EL4 cells or EL4 cells infected with HSVlac were negative for the B7.1 expression (FIGS. 12A&B). In contrast, approximately 95% of EL4 cells infected at an estimated MOI of 1 stained positively for B7.1 expression (FIG. 12C). On a per cell basis, HSV-B7.1 amplicon virus infected cells showed significantly higher levels of B7.1 expression than those observed for EL4-B7.1 cell line established by retroviral transduction. Expression of B7.1 in HSVB7.1 infected cells was maintained for up to 60 hours post-infection.

EXAMPLE 25

The bioactivity of HSV vector-expressed B7.1 was studied in an in vitro proliferation assay. Murine T-cells were enriched using a murine T-cell enrichment column (R&D Systems). $10^5$ T-cells were incubated in the presence of $5 \times 10^4$ gamma-irradiated stimulator cells. EL4 or CHO cells infected with HSV-B7.1, were used as stimulator cells. Retrovirally transduced EL4-B7.1, or CHO-B7.1 (kindly provided by Dr. Peter Linsley) were used as a positive control for B7.1 expression and parental EL4 or CHO cells served as a negative controls. Stimulator cells were irradiated to a total of 7500 rads using a Cesium-gamma source. Either anti-CD3 antibody (2C11) used as a (2C11)1:50 dilution of the hybridoma cell culture supernatant, or phorbol myristate (10 ng/ml) with ionophore (0.1 ng/ml) were added and the cells were cultured for 3 days at 37° C. in 5% CO2 incubator. To assay for proliferative responses in these stimulated cells, triplicate cultures were labeled for 16 hours with 1 μCi $^3$H-thymidine (NEN, 2Ci/mmol, 1 μCi/0.2 ml, final concentration). Cells were harvested on glass fiber filters using a cell harvester (Packard Instruments) and the incorporated 33H-radioactivity was measured using a beta-counter (Packard Instruments). Results are expressed as the mean (of triplicate cultures)+/−with the standard deviation. T-cell proliferation index (normalized cpm) was determined as the ratio of $^3$H-thymidine incorporated in the stimulated versus unstimulated control cultures.

When stimulated with anti-CD3 antibody (2C11) or a mixture of phorbol myristate acetate (PMA) and ionophore to provide 'signal one,' a significant proliferative response was observed for T-cells cocultured with HSVB7.1, but not HSVlac infected stimulator cells. The B7.1-dependent T-cell proliferative response observed with the HSVB7.1 infected EL4 cells was comparable to that seen with the retrovirally transduced control stimulator cells EL4-B7.1 or CHO-B7.1.

EXAMPLE 26

EL4 cells were infected with HSVrantes or HSVlac amplicon at an MOI of 1. EL4 cells at $1 \times 10^6$ were adsorbed with the amplicon virus in a volume of 0.5 ml at 37° C., 5% $CO^2$ for 4 hours, then 0.5 ml of fresh medium was added and incubation continued for another 20 hours. Cell culture supernatants were harvested at the end of 24 hours and supernatants tested for RANTES in a sandwich ELISA using anti-RANTES antibody (R&D Systems) for RANTES capture of RANTES in the culture supernatants and biotinylated anti-RANTES (R&D Systems) for detection followed by alkaline phosphatase-conjugated avidin. Para-Nitrophenyl phosphate was used as a substrate and absorbance developed color read at 405 nm was read in a BIORAD ELISA reader. Serial two fold dilutions of standard recombinant human-RANTES (R&D Systems) in duplicates were run in parallel to quantitate the amount of RANTES in the culture supernatant of infected cells.

In uninfected EL4 cells or cells transduced with HSVlac, no detectable RANTES secretion was observed in culture supernatants. Cells infected with HSVrantes at an MOI of 0.5 produced 3.1 ng of RANTES/ml/24 hours/$10^6$ cells. The observed levels of RANTES were higher than those measured in pooled G418 selected retrovirally transduced EL4-RANTES cells which secreted RANTES at a concentration of 1.45 ng/ml/24 hours/106 cells.

EXAMPLE 27

Adult C57BL/6 (H-$2^b$) female mice (8 weeks old) were obtained from Charles River Laboratories (MA) and maintained at the Animal Facility, University of Rochester Medical Center. The mice were handled under an approved laboratory animal handling and care protocol. Mice (6–12 per group) were shaved on the dorsal side of the hind limb and were inoculated subcutaneously (sc) with $10^6$ viable EL4 cells infected ex vivo with HSVB7.1, HSVrantes, or HSVlac amplicon virus, or with uninfected EL4 cells. In some experiments $10^6$ uninfected EL4 cells were inoculated sc. contralaterally on the other hind limb at the same time. Tumor growth was measured every 2–3 days using a caliper and size reported in millimeters diameter (mm). Animals were sacrificed when the tumor size reached 22–23 mm.

Figure 13A:
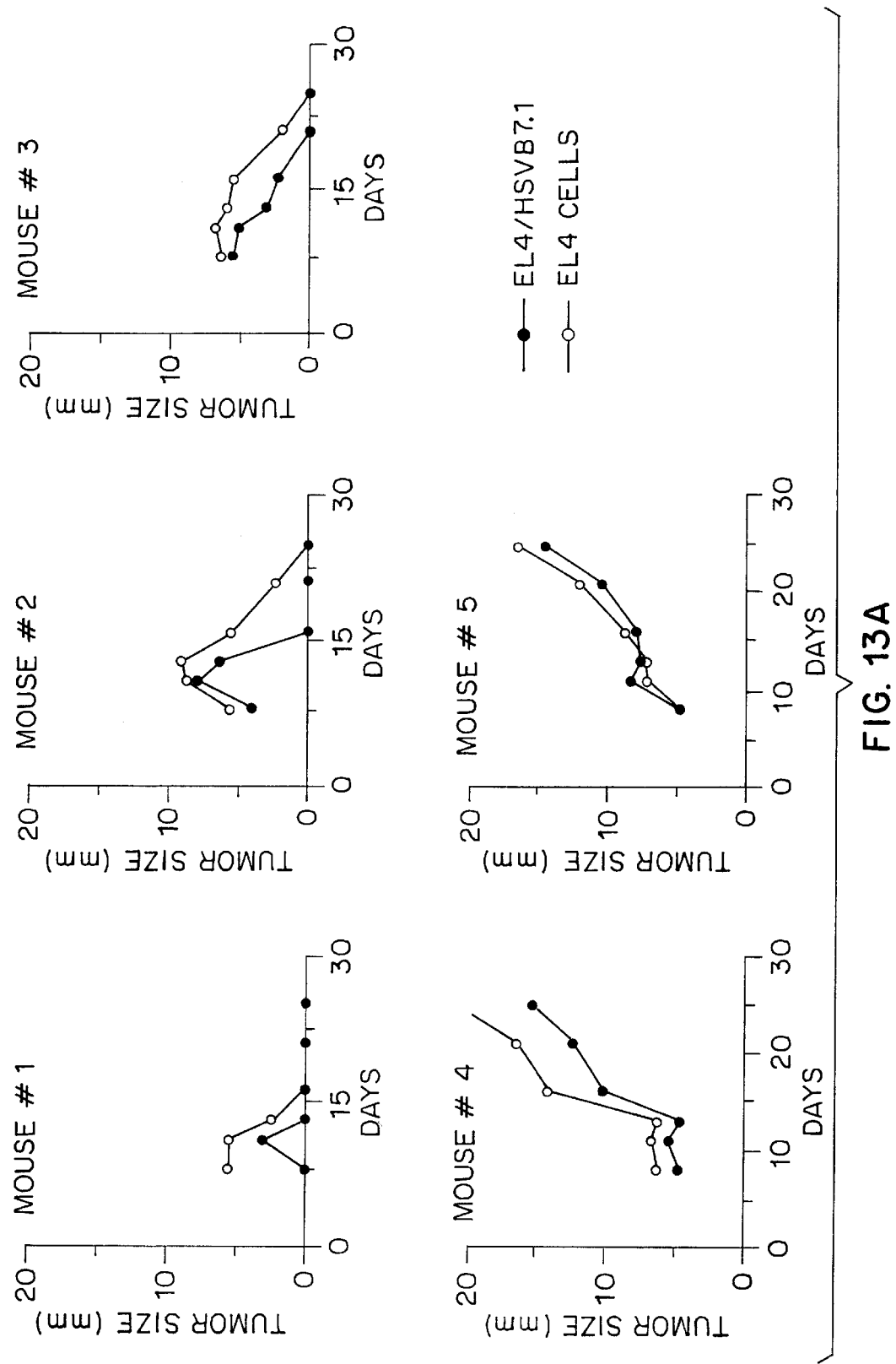
FIGS. 13A and B show tumor size in intratumorally-treated tumors and contralateral tumors, respectively.
Figure 13B:
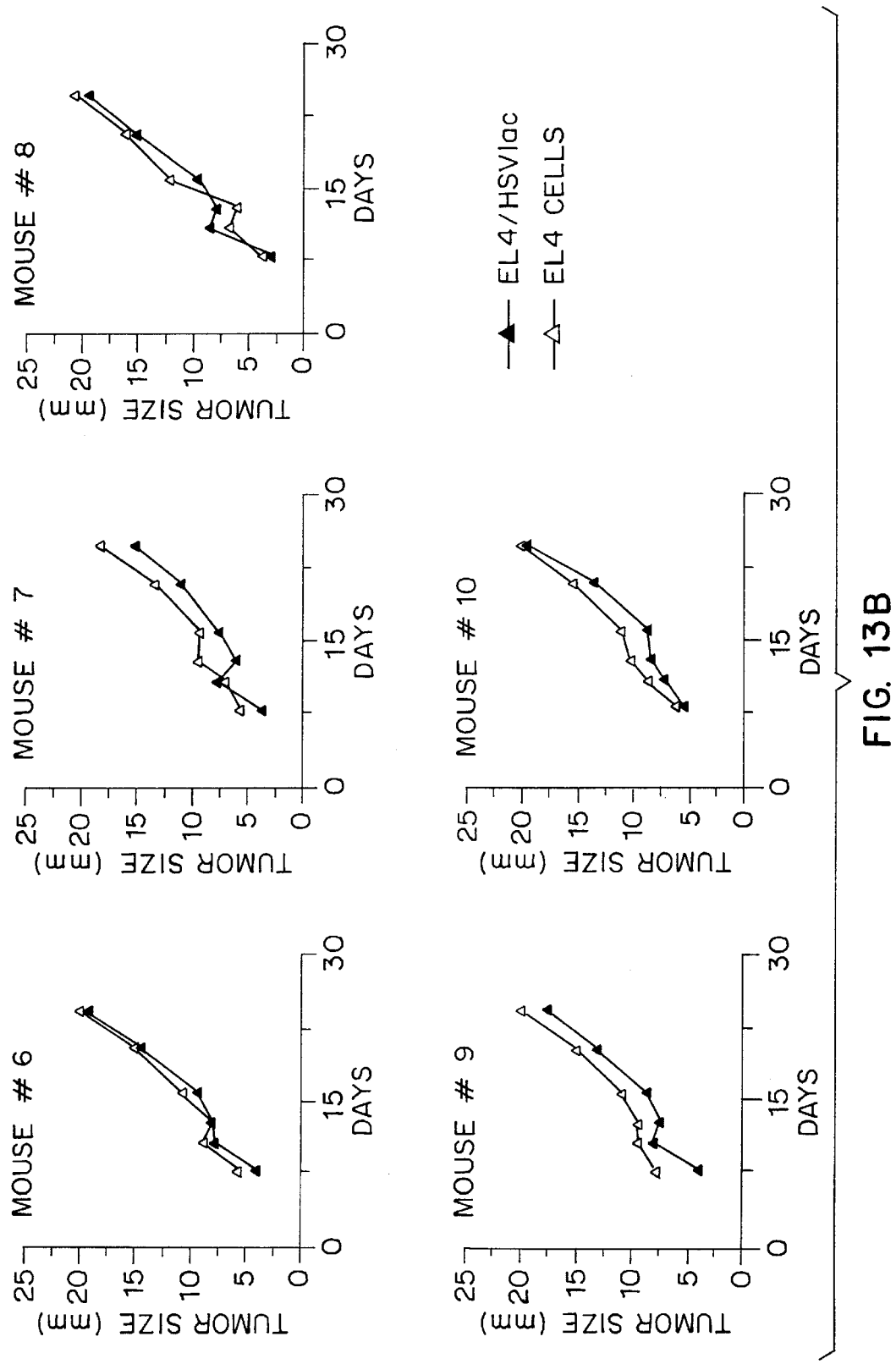
Figure 14A:
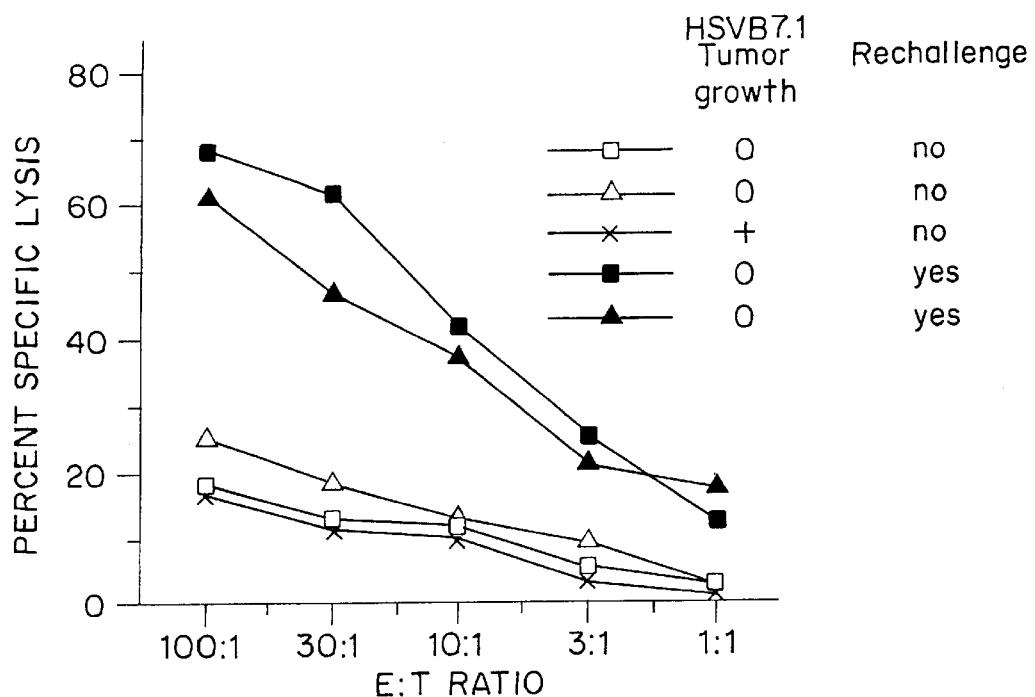
FIGS. 14A–D show CTL activity observed in splenocytes from mice receiving HSVB7.1 or HSVrantes alone or in combination, versus an HSVlac control.
Figure 14B:
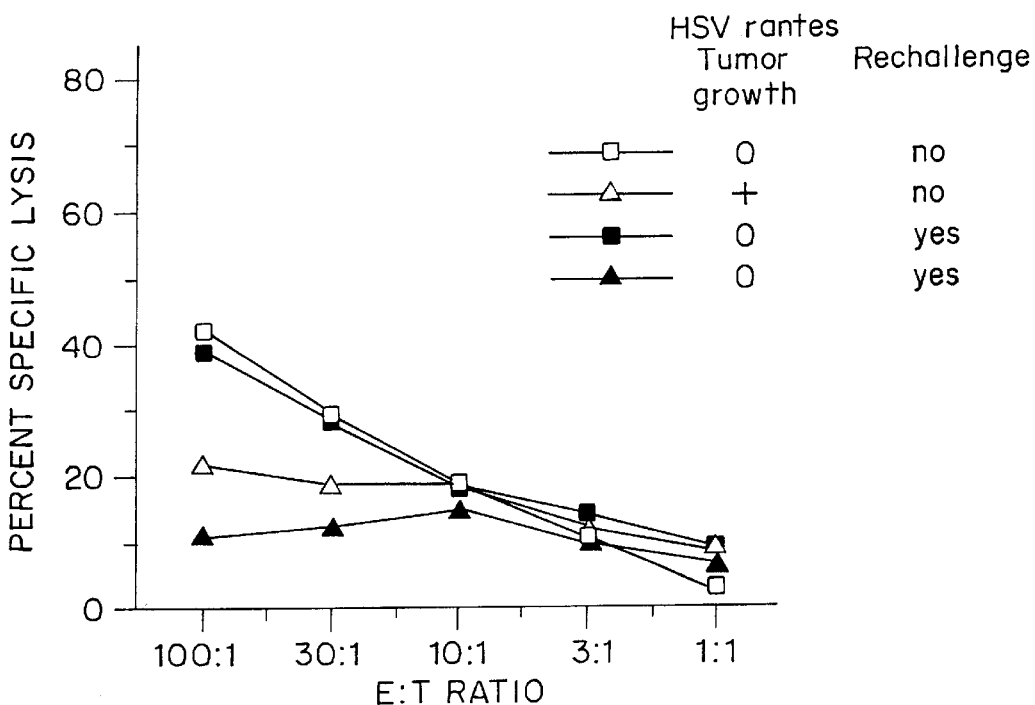
Figure 14C:
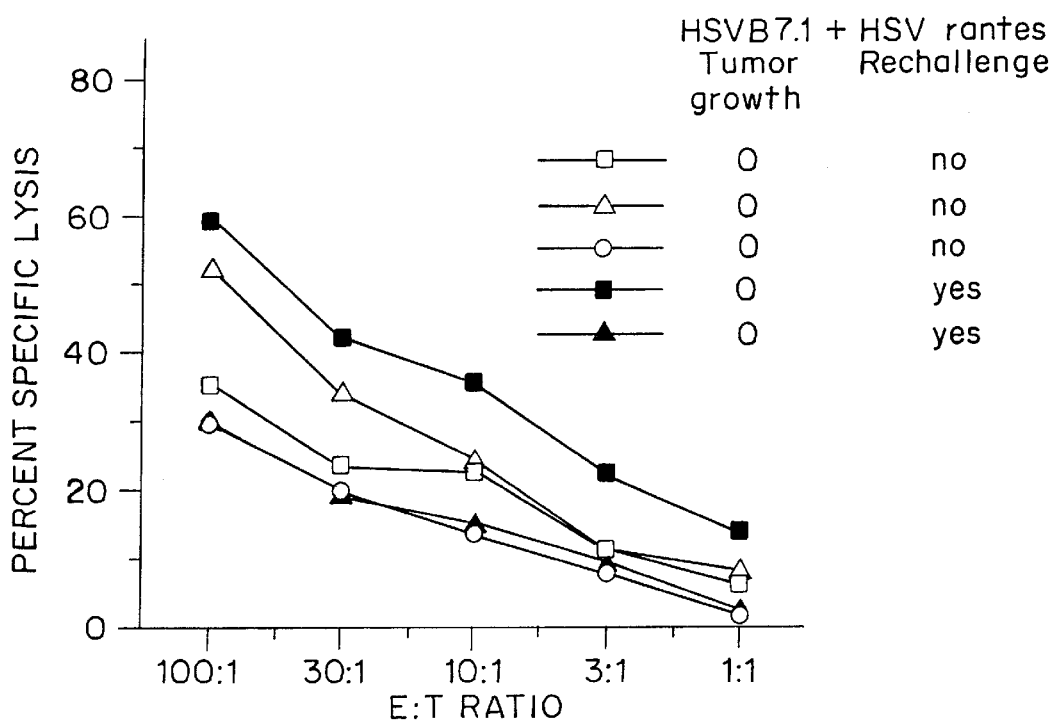
Figure 14D:
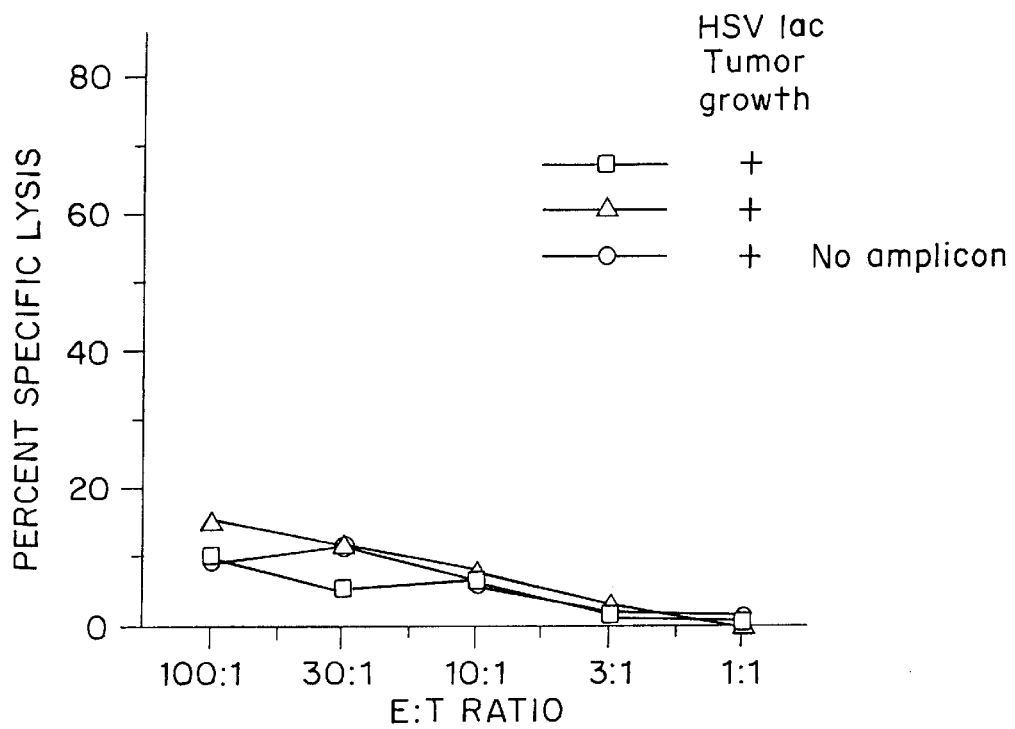

The results of these experiments on growth of HSV-infected EL4 cells and on contralateral EL4 tumors are summarized in Table 3 and FIGS. 13A and 13B. On day 20, complete regression of tumor was noted in 3/6 mice inoculated with EL4-HSVB7.1 transduced EL4 cells. Two of six mice inoculated with HSVrantes-transduced EL4 cells also showed initial tumor growth followed by complete regression in mice inoculated with EL4 infected with HSV-RANTES. When EL4 cells were infected with both HSVB7.1 and HSVrantes, 5/6 mice showed complete regression following initial tumor growth. Control EL4 cells or EL4 cells infected with the HSVlac vector grew tumor in 100% of the mice (6/6). Stably transduced EL4-B7.1 cells showed no evidence of tumor growth in all mice by day 20. These results support the conclusion that HSVB7.1 or HSVrantes amplicon infected cells were rejected due to a tumor specific immune response.

Similar results were observed in the experiment to evaluate whether inoculation of HSV vector transduced cells would inhibit growth of concurrent contralaterally inoculated parental non-transduced EL4 cells. In 3/5 mice, regression of ex vivo HSVB7.1 infected EL4 tumor was concordant with regression of the contralateral EL4 tumor (FIG. 13A). Both HSVlac infected EL4 cells and contralateral parental EL4 cells developed into tumor in 5/5 animals studied (FIG. 13B). These data support the conclusion that systemic tumor specific immunity to parental EL4 cells had developed in a subset of mice inoculated with EL4-HSVB7.1 transduced EL4 cells.

To test the efficacy of HSVB7.1 and HSVrantes on pre-established tumors using intratumoral inoculation of the HSV amplicons, $10^6$ viable EL4 cells were inoculated sc. on the dorsal side of the shaved hind limb and the tumor allowed to grow to a size of 5–6 mm (6–7 days). At this point the mice were grouped and either HSVB7.1, HSVrantes, HSVB7.1+HSVrantes, or HSVlac amplicon virus diluted in PBS to a concentration of $2 \times 10^6$ amplicon containing virus particles in 50 $\mu$l was inoculated intratumorally (10–12 mice/group). Control animals with pre-established EL4 tumor received only the diluent PBS. A second inoculation of the HSV amplicons was given on day 14, and the tumor growth was measured every 2–3 days. Tumors were allowed to grow to a maximal size of 22–23 mm size at which point the animals were sacrificed.

Complete tumor regression was observed in 17/26 mice injected with HSVB7.1 vector alone, in 11/22 mice injected with HSVrantes, and in 23/26 mice injected with the combination of HSVB7.1 and HSVrantes. Results of three independent experiments yielded similar results as summarized in Table 4.

To determine whether regression of tumor correlated with the development of systemic and memory T-cell immunity, mice manifesting complete tumor regression were rechallenged with parental EL4 cells in the on the other hind limb contralateral to the primary inoculation. All mice the rechallenged with parental EL4 cells showed no tumor growth (Table 4), thus indicating that tumor specific immunity was established by the antecedent direct intratumoral delivery of HSVB7.1 and/or HSVrantes into pre-established tumors.

EXAMPLE 28

To examine the induction of CTL responses in mice transduced intratumorally with the HSV amplicon vectors, splenocytes from the mice of Example 27 were evaluated. Spleens were harvested from C57BL/6 mice which had been inoculated with EL4 cells and injected intratumorally with either HSVB7.1 or HSVrantes alone or in combination. Control splenocytes were obtained from mice which were inoculated intratumorally with HSVlac virus or mice with PBS diluent alone. Splenocytes were prepared according to standard procedures and red blood cells lysed using AKC lysis buffer. To obtain cytolytic T-cells, splenocyte cell suspensions ($2 \times 1066$/ml in RP-10) were cultured together with gamma-irradiated (7500 rads) EL4 cells ($0.5 \times 10^6$ cells/ml) in a 25 $cm^2$ flask at 5% $CO_2$, 37° C. for 6 days. These in vitro cocultured splenocytes were then used as effector cells in the CTL assays. On the day of assay, EL4 target cells were washed with PBS and resuspended in RP10 medium (0.1 ml) at a concentration of $1.5–2 \times 10^6$ cells/ml and $Na^{51}CrO_4$ (NEN, 100 $\mu$Ci; stock concentration 1 mCi/ml) added for 90 minutes at 37° C. These cells were washed three times with PBS, resuspended in 1 ml RP-10 and viable cell count taken using a haemocytometer. $^{51}$Cr-labeled target cells ($10^4$ cells/0.1 ml) were added to the wells of a V-shaped 96 well plate, and three-fold serial dilutions of effector cells were made in triplicate, resulting in final effector-target cell ratios (E:T ratios) of 100:1, 33:1, 11:1 3:1, and 1:1. Spontaneous release of radioactivity from labeled target cells was measured by culturing the target cells with medium alone in six wells. Total release of radioactivity was determined by lysing the target cells with 2% Triton-X 100 detergent. Plates were spun at 1K for 2 minutes and incubated for 4 hrs at 37° C., 5% $CO_2$. The plates were then centrifuged at 2K for 4 minutes and half of the culture supernatant (100 $\mu$l) was counted for $^{51}$Cr release in a gamma counter (Packard Instrument). Mean values are calculated for the replicate wells and the results are expressed as % specific lysis according to the formula:

$$\% \text{ specific lysis} = 100 \times \frac{\text{experimental counts} - \text{spontaneous counts}}{\text{total counts} - \text{spontaneous counts}}$$

The mean spontaneous release for virus-infected and uninfected controls averaged between 10 to 20% of the total counts.

Significant specific CTL activity was seen in splenocytes from mice receiving HSVB7.1 or HSVrantes alone or in combination (FIGS. 14A-D) CTL responses were only seen in mice in which EL4 tumor regressed after direct delivery of the HSVB7.1 and/or HSVrantes amplicons into pre-established tumor. Levels of CTL activity were greater in mice which received both the HSVB7.1 and HSVrantes vectors. The highest levels of CTL activity were observed in mice which had been rechallenged with the parental EL4 cells.

REFERENCES

The following references are cited herein and are incorporated herein by reference.

BERGOLD P. J., CASACCIA-BONNEFIL P., XIU-LIU Z. & FEDEROFF H. J. (1993) Transsynaptic neuronal loss induced in hippocampal slice cultures by a herpes simplex virus vector expressing the GluR6 subunit of kainate receptor. *Proc. Natl. Acad. Sci. U.S.A.* 90, 6165–6169.

DANNENBERG A. M. & SUGA M. (1981) Histochemical stains for macrophages in cell smears and tissue sections: β-galactosidase, acid phophatase, nonspecific esterase, succinic dehydrogenase, and cytochrome oxidase. In *Methods for studying mononuclear phagocytes*. Eds D. O. Adams, P. J. Edelson & M. S. Koren. New York: Academic Press. pp. 282–284.

DAVIDSON B. L., ALLEN E. D., KOZARSKY K. F., WILSON J. M. & ROESSLER B. J. (1993) A model system for in vivo gene transfer into the central nervous system using an adenoviral vector. *Nat. Genet.* 3, 219–223.

DRANOFF G., JAFFEE E., LAZENBY A., GOLUMBEK P., LEVITTSKY H., BROSE K., JACKSON V., HAMADA H., PARDOLL D. & MULLIGAN R. C. (1993) Vaccination with irradiated tumor cells engineered to secrete murine granulocyte-macrophage colony-stimulating factor stimulates potent, specific, and long-lasting immunity. *Proc. Natl. Acad. Sci. USA* 90, 3539–3543.

DRAZAN K. E., SHEN X. D., CSETE M. E., ZHANG W. W., ROTH J. A., BUSUTTIL R. W. & SHAKED A. (1994) In vivo adenoviral-mediated human p53 tumor suppressor gene transfer and expression in rat liver after resection. *Surgery* 116, 197–204.

ENGVALL E., PIHKO H., JALANKO H. & RUOSLAHTI E. (1977) Effect of specific immunotherapy with preimmunization against alpha-fetoprotein on a mouse transplantable hepatoma. *J N. C. I.* 59, 277–280.

FEDEROFF H. J. (1996) Growth of replication defective herpes virus amplicon vectors and their use for gene transfer. In *Cell Biology: a Laboratory Manual*. Eds D. L. Spector, L. Leinwand & R. Goldman.

GANSBACHER B., ZIER K., CRONIN K., HANTZOPOULOS P. A., BOUCHARD B., HOUGHTON A., GILBOA E. & GOLDE D. (1992) Retroviral gene transfer induced constitutive expression of interleukin-2 or interferon-gamma in irradiated human melanoma cells. *Blood.* 80, 2817–2825.

GELLER A. I. & BREAKEFIELD X. O. (1988) A defective HSV-1 vector expresses *Escherichia coli* β-galactosidase in cultured peripheral neurons. *Science* 241, 1667–1669.

GELLER, A. I., KEYOMARSI, K., BRYAN, J. & PARDEE, A. B. (1990) An efficient deletion mutant packaging system for defective herpes simplex virus vectors: Potential application to human gene therapy and neuronal packaging. *Proc. Nat'l Acad. Sci.* (USA) 87, 8950–8954.

GELLER A. I. & FEDEROFF H. J. (1991) The use of HSV-1 vectors to introduce heterologous genes into neurons: implications for gene therapy. In *Human gene transfer*. Eds O. Cohen-Haguenauer & M. Botron. London: John Libbey Eurotext Ltd. pp. 63–73.

GESCHWIND M., LU B. & FEDEROFF H. J. (1994) Expression of neurotrophic genes from herpes simplex virus type I vectors modifying neuronal phenotype. In *Providing Pharmacological Access to the Brain: Alternative Approaches*. Eds T. R. Flanagan, D. F. Emerich & S. R. Winn. New York: Academic Press. pp. 462–482.

JARNAGIN W. R., DEBS R. J., WANG S. S. & BISSELL D. M. (1992) Cationic lipid-mediated transfection of liver cells in primary culture. *Nucleic. Acids. Res.* 20, 4205–4211.

JOHNSON P., MIYANOHARA A., LEVINE F., CAHILL T. & FRIEDMANN T. (1992) Cytotoxicity of a replication-defective mutant of herpes simplex virus type I. *J Virol* 66, 2952–2965.

LEIB D. A. & OLIVO P. D. (1993) Gene therapy to neurons: is herpes simplex virus the right tool for the job? *BioEssays* 15, 547–554.

LINNIK M., ZAHOS P., GESCHWIND M. & FEDEROFF H. (1995) Expression of bcl-2 from a defective herpes simplex virus-I vector limits neuronal death in focal cerebral ischemia. *Stroke* 26, 1670–1675.

LOTZE M. T., RUBIN J. T., CARTY S., EDINGTON H., FERSON P., LANDRENEAU R., PIPPIN B., POSNER M., ROSENFELDER D., WATSON C., CARLOS T., KIRKWOOD J., LEMBERSKY B., LOGAN T., ROSENSTEIN M., RYBACK M. E., WHITESIDE T., ELDER E., MOEN R. C., JACOB W., CHEN Y., PINKUS R. L. & BRYANT J. (1994) Clinical protocol: Gnee therapy of cancer: a pilot study of IL-4-gene-modified fibroblasts admixed with autologous tumor to elicit an immune response. *Hum. Gene. Ther.* 5, 41–55.

MIKI, I, ISHIHARA, N., OTOSHI, M. & KASE, H., *The Journal of Immunological Methods* 164: 255–261 (1993).

PAQUEREAU L. & LE CAM A. (1992) Electroporation-mediated gene transfer into hepatocytes: preservation of a growth hormone response. *Anal. Biochem.* 204, 147–151.

PATEL P. M., FLEMMING C. L., FISHER C., PORTER C. D., THOMAS J. M., GORE M. E. & COLLINS M. K. L. (1994) Generation of interleukin-2-secreting melanoma cell populations from resected metastatic tumors. *Hum. Gene. Ther.* 5, 577–584.

PATERSON T. & EVERETT R. A. (1990) A prominent serine-rich region in Vmwl 75, the major transcriptional regulator protein of herpes simplex virus type 1, is not essential for virus growth in tissue culture. *J Gen Virol* 71, 1775–1783.

PORGADOR A., BANNERJI R., WATANABE Y., FELDMAN M., GILBOA E. & EISENBACH L. (1993) Antimetastatic vaccination of tumor-bearing mice with two types of IFN-gamrnma gene-inserted tumor cells. *J. Immunol.* 150, 1458–1470.

ROSENBERG S. A., ANDERSON W. F., BLAESE M. R., ETTINGHAUSEN S. E., HWU P., KARP S. E., KASID A., MULE J. J., PARKINSON D. R., SALO J. C., SCHWARTRUBER D. J., TOPALIAN S. L., WEBER J. S., YANNELLI J. R., YANG J. C. & LINEHAN W. M. (1992) Initial proposal of clinical research project: Immunization of cancer patients using autologous cancer cells modified by insertion of the gene for interleukin-2. *Hum. Gene. Ther.* 3, 75–90.

SAITO S., BANNERJI R., GANSBACHER B., ROSENTHAL F. M., ROMANENKO P., HESTON W. D. W., FAIR W. R. & GILBOA E. (1994) Immunotherapy of bladder cancer with cytokine gene-modified tumor vaccines. *Cancer Res.* 54, 3516–3520.

SEIGLER H. F., DARROW T. L., ABDEL-WAHAB Z., GANGAVALLI R. & BARBER J. (1994) Clinical protocol: a phase I trial of human gamma interferon transduced autologous tumor cells in patients with disseminated malignant melanoma. *Hum. Gene. Ther.* 5, 761–777.

WILSON J. M., JEFFERSON D. M., CHOWDHURY J. R., NOVIKOFF P. M., JOHNSTON D. E. & MULLIGAN R. C. (1988) Retrovirus-mediated transduction of adult hepatocytes. *Proc Natl. Acad. Sci. U.S.A.* 85, 3014–3018.

XU H., FEDEROFF H., MARAGOS J., PARADA L. & KESSLER J. (1994) Viral transduction of trk A into cultured nodose and spinal motor neurons conveys NGF responsiveness. *Dev Biol* 163, 152–161.

YANG J., TSUKAMOTO T., POPNIKOLOV N., GUZMAN R. C., CHEN X., YANG J. H. & NANDI S. (1995) Adenoviral-mediated gene transfer into primary human and mouse mammary epithelial cells in vitro and in vivo. *Cancer Letters*. 98, 9–17.

ZIER K. (1982) Functional and antigenic properties of cultured T cells in the cell mediated lympholysis (CML) assay. *Hum. Immunol.* 4, 147–152.

TABLE 1

Efficiency of IL-2 Secretion from Human Tumor Cells Transduced with HSVil2

| Patient | Diagnosis | | | MOI | | |
|---|---|---|---|---|---|---|
| | Clinical | Histologic | Radiation | 0 | 0.5 | 1 | 2 |
| 1 | Met Colorectal Ca | Moderately differentiated Adenocarcinoma | No | 0 | 580 ± 40 | 6400 ± 200 | 10700 ± 70 |
| | | | Yes | 0 | 334 ± 4 | 5500 ± 100 | 10500 ± 50 |
| 2 | Hepatoma | Clear cell adenocarcinoma | No | 0 | 2100 ± 10 | 2600 ± 20 | 5900 ± 70 |
| | | | Yes | 0 | 580 ± 40 | 2490 ± 40 | 6450 ± 70 |
| 3 | Gallbladder Ca | Moderately differentiated Adenocarcinoma | No | 0 | ND | 12500 ± 700 | ND |
| | | | Yes | 0 | ND | 4800 ± 100 | ND |
| 4 | Hepatoma | Poorly differentiated Adenocarcinoma | No | 0 | ND | 17500 ± 500 | ND |
| | | | Yes | 0 | ND | 19300 ± 600 | ND |

ND, not determined. Values are mean levels of samples transduced in quadraplicate ± SEM. Levels are $pg/10^6$ cells/24 hours.

TABLE 2

Effect of timing of irradiation and HSV exposure on cell viability. Hepatoma cells were either exposed to radiation (10,000 rads) followed by a 20 minute exposure to HSV (Rad/USV), or exposed to HSV for 20 minutes followed by irradiation (10,000 rads) (HSV/Rad). Cells ($5 \times 10^5$ cells were then plated and left in culture for 48 hours. Non-viable cells were washed off before harvesting cells for counting. In addition, harvested cells were verified to be viable by trypan blue exclusion. Comparisons were by student's: t-test.

| MOI | Rad/HSV ($\times 10^5$ cells) | HSV/Rad ($\times 10^5$ cells) | p |
|---|---|---|---|
| 0 | 2.1 ± 0.1 | 1.8 ± 0.2 | 0.1 |
| 0.5 | 2.0 ± 0.1 | 1.8 ± 0.2 | 0.2 |
| 1.0 | 1.8 ± 0.1 | 1.5 ± 0.1 | 0.2 |

TABLE 3

Tumor growth of EL4 cells infected ex vivo with HSV amplicons. EL4 cells were infected in vitro with HSV amplicon virus and maintained in culture for 8 hours. $10^6$ viable HSV amplicon infected EL4 cells were inoculated s.c. in mice and tumor presence at one month recorded.

| HSV amplicon | # of mice with tumor/ # of mice inoculated |
|---|---|
| HSV-B7.1 | 3/6 |
| HSV-RANTES | 4/6 |
| HSV-B7.1 & HSV-RANTES | 1/6 |
| HSV-LacZ | 6/6 |

TABLE 4

Intratumoral delivery of HSV amplicons into pre-established EL4 tumors. EL4 cells were inoculated s.c. in mice and tumors allowed to develop to a 5–6 mm diameter. HSV amplicon virus was inoculated in two doses, on days 7 and 14, and tumor growth monitored and recorded after one month. The values reported correspond to the number of mice with tumor/total number of mice.

| HSV amplicon | Primary Tumor Growth | Tumor Growth Following Rechallenge |
|---|---|---|
| Experiment #1 | | |
| HSVB7.1 | 1/4 | 0/3 |
| HSVB7.1 ± HSVrantes | 0/4 | 0/4 |
| HSVlac | 4/4 | |
| Experiment #2 | | |
| HSVB7.1 | 4/10 | 0/6 |
| HSVrantes | 5/10 | 0/5 |
| HSVB7.1 ± HSVrantes | 1/10 | 0/9 |
| HSVlac | 5/5 | |
| Experiment #3 | | |
| HSVB7.1 | 4/12 | 0/4 |
| HSVrantes | 6/12 | 0/4 |
| HSVB7.1 ± HSVrantes | 2/12 | 0/6 |
| HSVlac | 5/5 | |

We claim:

1. A method for production of an autologous vaccine to tumor cells comprising transducing the tumor cells with a herpes simiplex virus amplicon containing the gene for an immunostimulatory protein to provide transient expression of the immunostimulatory protein by the cells, wherein the immunostimulatory protein is selected from the group consisting of cytokines, including chemokines, intercellular adhesion molecules, and costimulatory molecules necessary for the activation of B or T cells.

2. The method according to claim 1, wherein the tumor cells are transduced with the herpes simplex amplicon ex vivo.

3. The method according to claim 1, wherein the tumor cells are transduced with the herpes simplex amplicon in vivo.

4. The method according to claim 1, wherein the immunostimulatory protein is a cytokine.

5. The method according to claim 4, wherein the cytokine is interleukin-2.

6. The method according to claim 4, wherein the cytokine is granulocyte macrophage colony stimulating factor.

7. The method according to claim 4, wherein the immunostimulatory protein is a chemokine.

8. The method according to claim 7, wherein the chemokine is RANTES.

9. The method according to claim 1, wherein the immunostimulatory protein is a intercellular adhesion molecule.

10. The method according to claim 9, wherein the intercellular adhesion molecule is ICAM-1.

11. The method according to claim 1, wherein the immunostimulatory protein is a costimulatory factor.

12. The method according to claim 11, wherein the costimulatory factor is B7.1.

13. The method according to claim 1, wherein a population of tumor cells is transduced with one or more species of amplicon comprising more than one kind of immunostimulatory protein gene and expressing more than one kind of immunostimulatory protein.

14. The method according to claim 13, wherein the tumor cells are transduced with amplicons encoding and expressing at least two species of cytokines.

15. The method according to claim 14, wherein tumor cells are transduced with amplicons comprising interleukin-2 and interleukin-12 genes.

16. The method according to claim 13, wherein the tumor cells are transduced with amplicons encoding and expressing a cytokine and a costimulatory factor.

17. The method according to claim 16, wherein tumor cells are transduced with amplicons comprising RANTES and B7.1 genes.

18. The method according to claim 1, wherein the tumor cells are hepatoma cells or lymphoma cells.

19. A method for inducing a protective immune response to tumor cells in a patient comprising the step of transducing the tumor cells with a herpes simplex virus amplicon comprising an immunostimulatory protein gene to provide transient expression of the immunostimulatory protein by the cells, wherein the immunostimulatory protein is selected from the group consisting of cytokines, including chemokines, intercellular adhesion molecules, and costimulatoly molecules necessary for the activation of B or T cells.

20. The method according to claim 19, wherein the tumor cells are transduced with the amplicon ex vivo, further comprising the step of introducing the transduced tumor cells into the patient.

21. The method according to claim 19, wherein the amplicon is injected into the site of the tumor cells in vivo.

22. The method according to claim 19, wherein the immunostimulatory protein is a cytokine.

23. The method according to claim 22, wherein the cytokine is interleukin-2.

24. The method according to claim 22, wherein the cytokine is granulocyte macrophage colony stimulating factor.

25. The method according to claim 22, wherein the immunostimulatory protein is a chemokine.

26. The method according to claim 25, wherein the chemokine is RANTES.

27. The method acording to claim 19, wherein the immunostimulatory protein is a intercellular adhesion molecule.

28. The method according to claim 27, wherein the intercellular adhesion molecule is ICAM-1.

29. The method according to claim 19, wherein the immunostimulatory protein is a costimulatory factor.

30. The method according to claim 29, wherein the costimulatory factor is B7.1.

31. The method according to claimi 9, wherein a population of tumor cells is transduced with one or more species of amplicon comprising more than one kind of immunostimulatory protein gene and expressing more than one kind of immunostimulatory protein.

32. The method according to claim 31, wherein the tumor cells are transduced with amplicons encoding and expressing at least two species of cytokines.

33. The method according to claim 32, wherein tumor cells are transduced with amplicons comprising interleukin-2 and interleukin-12 genes.

34. The method according to claim 31, wherein the tumor cells are transduced with amplicons encoding and expressing a cytokine and a costimulatory factor.

35. The method according to claim 34, wherein tumor cells are transduced with amplicons comprising RANTES and B7.1 genes.

36. The method according to claim 19, wherein the tumor cells are hepatoma cells or lymphoma cells.

37. A method for production of an autologous vaccine to tumor cells comprising transducing the tumor cells with one or more species of herpes simplex virus amplicon comprising an immunostimulatory protein gene and at least one additional therapeutic gene to provide transient expression of the immunostimulatory protein and the therapeutic gene product by the cells, wherein the imnunostimulatory protein is selected from the group consisting of cytokines, including chemokines, intercellular adhesion molecules, and costimulatory molecules necessary for the activation of B or T cells.

38. The method according to claim 37, wherein the tumor cells are transduced with the herpes simplex amplicons ex vivo.

39. The method according to claim 37, wherein the tumor cells are transduced with the herpes simplex cell in vivo.

40. A method for inducing a protective immune response to tumor cells in a patient comprising the step of transducing the tumor cells with one or more species of herpes simplex virus amplicon comprising an immunostimulatory protein gene and at least one additional therapeutic gene to provide transient expression of the immunostimulatory protein and the therapeutic gene product by the cells, wherein the immunostimulatory protein is selected from the group consisting of cytokines, including chemokines, intercellular adhesion molecules, and costimulatory molecules necessary for the activation of B or T cells.

* * * * *